(12) United States Patent
Yagoshi

(10) Patent No.: US 12,120,997 B2
(45) Date of Patent: Oct. 22, 2024

(54) PURPLE BABY BROCCOLI

(71) Applicant: SAKATA SEED AMERICA, INC., Morgan Hill, CA (US)

(72) Inventor: Tsunehiro Yagoshi, Kakegawa (JP)

(73) Assignee: Sakata Seed America, Inc., Woodland, CA (US)

( * ) Notice: Subject to any disclaimer, the term of this patent is extended or adjusted under 35 U.S.C. 154(b) by 499 days.

(21) Appl. No.: 16/916,424

(22) Filed: Jun. 30, 2020

(65) Prior Publication Data
US 2020/0329657 A1    Oct. 22, 2020

Related U.S. Application Data

(62) Division of application No. 15/344,339, filed on Nov. 4, 2016, now Pat. No. 11,019,781.

(51) Int. Cl.
| | |
|---|---|
| *A01H 1/00* | (2006.01) |
| *A01H 5/02* | (2018.01) |
| *A01H 5/10* | (2018.01) |
| *A01H 6/20* | (2018.01) |

(52) U.S. Cl.
CPC ............. *A01H 6/203* (2018.05); *A01H 1/00* (2013.01); *A01H 5/02* (2013.01); *A01H 5/10* (2013.01)

(58) Field of Classification Search
None
See application file for complete search history.

(56) References Cited

U.S. PATENT DOCUMENTS

| | | |
|---|---|---|
| 5,254,802 A | 10/1993 | Hoekstra et al. |
| 5,523,520 A | 6/1996 | Hunsperger et al. |
| 6,274,793 B1 | 8/2001 | Kobayashi et al. |
| 11,019,781 B2 | 6/2021 | Yagoshi |
| 2011/0265201 A1 | 10/2011 | Van Den Bosch et al. |
| 2012/0324596 A1 | 12/2012 | Mero |
| 2017/0071147 A1 | 3/2017 | Yagoshi |

FOREIGN PATENT DOCUMENTS

| | | |
|---|---|---|
| AU | 2017355483 | 7/2018 |
| CN | 103168681 B | 8/2014 |
| CN | 103975849 B | 6/2016 |
| WO | PCT/US2017/059916 | 1/2018 |
| WO | WO-2018/085646 A1 | 5/2018 |

OTHER PUBLICATIONS

Bennetzen, et al., 1992, Approaches and progress in the molecular cloning of plant disease resistance genes, Genetic Engineering, 14:99-124, Ed. J.K. Setlow, Plenum Press, NY.
Cheung, et al., 1997, Conservation of S-locus for self incompatibility in *Brassica napus* (L.) and *Brassica oleracea* (L.), Theor. Appl. Genet., 95:73-82.
Earle, et al., 1994, Cold-tolerant Ogura CMS *Brassica* vegetables for horticultural use, Cruciferase Newsletter, 16:80-81.
Eshed, et al., 1996, Less-than-additive epistatic interactions of quantitative trait loci in tomato, Genetics, 143:1807-1817.
Kott, et al., 1990, The role of biotechnology in canola/rapeseed research, Rapeseed Production, Nutrition, and Technology, pp. 47-78, Van Reinhold, NY.
Kraft, et al., 2000, Linkage disequilibrium and fingerprinting in sugar beet, Theor. App. Genet., 101:323-326.
Lim, T.K., 2014, *Brassica oleracea* italica x alboglabra. Edible Medicinal and Non-Medicinal Plants: vol. 7, Flowers, pp. 624-627.
Martin et al., Jun. 2012, Survival and Yields of Fall-planted Winter Sprouting Broccoli Grown in High Tunnels for Spring Harvest in the Northeastern United States, HortTechnology, vol. 22, No. 3, pp. 345-352.
Pang, et al., 1992, Expression of a gene encoding a scorpion insectotoxin peptide in yeast, bacteria and plants, Gene, 116:165-172.
Poehlman, J.M. and Sleper, D.A., Breeding Field Crops, 4th Ed. (1995), Iowa State University Press, Ames, Iowa, p. 473.
www.sakatavegetables.com/index.cfm/fuseaction/HGplants.plantDetail/plant_id/424/index.htm, Aspabroc (Hybrid) Baby Broccoli, 2 pages, retrieved from the internet on Jan. 12, 2017.
http://agsyst.wsu.edu/Broccolini.html, Broccolini®, 2 pages, retrieved from the internet on Jan. 12, 2017.
www.specialtyproduce.com/produce/Broccolini_Aspirations_444.php, Broccolini (Aspirations), 1 page, retrieved from the internet Jan. 12, 2017.
https://myfolia.com/plants/149-broccoli-brassica-oleracea-italica-group/varieties/133457-santee-f1, Broccoli 'Santee F1', 3 pages, retrieved from the internet on Jan. 12, 2017.
http://www.territorialseed.com/product/purple-peacock-broccoli-seed, Purple Peacock Broccoli Organic, 2 pages, retrieved from the internet on Jan. 12, 2017.
http://www.specialtyproduce.com/produce/Purple_Peacock_Broccoli_11830.php, Purple Peacock Broccoli, 1 page, retrieved from the internet on Jan. 12, 2017.

(Continued)

*Primary Examiner* — Phuong T Bui
(74) *Attorney, Agent, or Firm* — Weatherly IP Solutions, LLC; James M. Weatherly

(57) ABSTRACT

Purple baby broccoli plants and methods for producing purple baby broccoli plants are disclosed. The invention relates to the plants and seeds of purple baby broccoli and to methods for producing a *Brassica oleracea* plant having purple head and purple stems plant by crossing the purple baby broccoli with itself or another cultivar. The invention further relates to the parents of purple baby broccoli and for methods of producing purple baby broccoli. The invention also relates to methods for producing locus conversion plants of purple baby broccoli and its parent plants and to the plants produced by those methods. This invention also relates to *Brassica oleracea* cultivars or breeding cultivars and plant parts derived from purple baby broccoli, to methods for producing other *Brassica oleracea* cultivars, lines or plant parts derived from purple baby broccoli and to the *Brassica oleracea* plants, varieties, and their parts derived from the use of those methods.

2 Claims, No Drawings

(56) References Cited

OTHER PUBLICATIONS https://myfolia.com/plants/149-broccoli-brassica-oleracea-italica-group/varieties/5205-purple-peacock, Broccoli 'Purple Peacock', 4 pages, retrieved from the internet on Jan. 12, 2017.
http://www.territorialseed.com/product/summer-purple-broccoli-seed/broccoli_seed, Summer Purple Broccoli, 2 pages, retrieved from the internet on Jan. 12, 2017.
https://specialtyproduce.com/produce/Purple_Peacock_Broccoli_11830.php; 1 page, retrieved from the internet Apr. 12, 2023.
https://sakatahomegrown.com/homegrown/aspabroc/; 1 page, retrieved from the internet Apr. 11, 2023.
https://doc-10-38-apps-viewer.googleusercontent.com/viewer/secure/pdf/f3sagiula217dg151elr7rci9sill315/10411rtq9cm0ocv51cd1q9o1nhk1hopr/1680744000000/gmail/01659102238680445465/ACFrOgC25yjri5IcrwJBFNHzV8_OkFBjCdWB6RzBXRa8vRBWUwWHeEpMeEa_EOKUjdlCriKxflmTwH; 2 pages, retrieved from the internet Apr. 11, 2023.

PURPLE BABY BROCCOLI

CROSS REFERENCE TO RELATED APPLICATIONS

This application is a divisional of and claims the benefit of priority from U.S. patent application Ser. No. 15/344,339 filed on Nov. 4, 2016, which is incorporated herein by reference in its entirety.

BACKGROUND OF THE INVENTION

The present invention relates to the development of a new and distinct broccoli type (*Brassica oleracea*), designated purple baby broccoli, having purple stems, a tender texture and early maturity. The invention further relates to parent lines thereof, and methods of producing purple baby broccoli plants. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Broccoli is a member of the Brassicaceae family that is classified in the Italica cultivar group of the species *Brassica oleracea* and has a chromosome number of 2n=18. Broccoli is grown for its large, edible flower heads that are usually green in color and arranged in a tree-like fashion on branches sprouting out from a thick, edible stalk. Broccoli is a cool-weather crop that typically does poorly in hot summer weather. The flower head clusters are eaten before the flower buds open, and may be eaten raw, boiled, steamed, or cooked a variety of ways. Broccoli is a very nutritious vegetable that is high in vitamin C and vitamin K. In addition, broccoli contains multiple nutrients considered to have potent anti-cancer properties, including diindolymethane, selenium and glucoraphanin. There are three commonly grown types of broccoli: 1) Calabrese, which is the most familiar with large green heads and thick stalks, 2) Sprouting, which has a larger number of heads with many thin stalks, and 3) Romanesco, which has numerous small cone-shaped heads arranged in spirals and is yellow-green in color. White and purple varieties of broccoli are also available in some areas.

The introduction of hybrid broccoli cultivars in the 1960's provided a magnitude increase in yield, holding ability, plant uniformity, expanded growing seasons and large-scale production of broccoli. The goal in broccoli breeding is to make continued improvement in hybrid broccoli yields and horticultural characteristics in order to sustain the supply to meet continuous increase in demand for broccoli in developed and emerging world economies.

All *Brassica oleracea* will cross-pollinate. Pollination occurs via insect vectors, the most common of which is the honeybee. Broccoli, like most other Brassicas, has a genetic characteristic of self-incompatibility, which encourages cross pollination resulting in higher levels of variability. Variability in populations is desired for wide adaptation and survival. Broccoli breeding populations can be inbred or backcrossed and/or with the use of double haploids derived from anther culture to develop homozygous inbred lines. Broccoli $F_1$ hybrids can be produced by using self-incompatibility or cytoplasmic male sterility to control pollen movement between selected inbred lines.

Self-incompatibility (SI) is a breeding system that favors outcrossing and therefore maximizes recombination in cross-pollinated species. This breeding system in nature has been utilized by humans in $F_1$ hybrid breeding, especially in Brassica vegetables (Tsunoda et al., chapter 13). However, SI itself is not a satisfactory method for producing seed that is entirely or almost entirely hybrid.

Cytoplasmic male sterility (CMS) is another method used in Brassica vegetable species to produce $F_1$ hybrids. This method of producing hybrids in Brassica is a more recent development compared to self-incompatibility. A genetic mutation contained in the cytoplasm (mitochondria) is responsible for the lack of production of pollen. In Brassica, the cytoplasm has commonly been identified in and transferred from "Ogura" type radish (Ogura, 1968). The major advantage of CMS over self-incompatibility is that under normal conditions, no pollen is produced in the female parent. Theoretically, this results in the production of 100% hybrid seed. Under certain stressful growth conditions, however, it may be possible to produce small amounts of fertile pollen in CMS plants. Brassica inbreds containing CMS are maintained by continued hybridization to their normal (fertile) counterpart inbred, commonly referred to as "B" line or a maintainer line.

Baby broccoli is a hybrid of broccoli (*Brassica oleracea* L. var. *italica*) and gai-lan (*Brassica oleracea* var. *alboglabra*), also known as kai-lan, Chinese broccoli, or Chinese kale. Gai-lan is a leaf vegetable having thick, flat, glossy blue-green leaves with thick stems and a small number of tiny flower heads. Baby broccoli is a green vegetable similar to broccoli, but with smaller florets, longer thinner tender stalks, and a subtle sweet flavor with a peppery taste. It resembles a broccoli raab with an asparagus stem. Baby broccoli is known by the trade names Broccolini® and Aspabroc, as well as Asparation®, asparations, Bimi®, broccoletti, broccolette and Tenderstem™.

Baby broccoli was first developed in 1993 by Sakata Seed Company in Japan. Growing and harvesting baby broccoli has proved to be moderately challenging. Unlike broccoli, the side shoots of baby broccoli rather than the main stalk are harvested. The main stalk is removed as the plant begins to mature to enhance side shoot development. Whereas broccoli is harvested three times during a season, baby broccoli may be harvested three to five times, depending on growing conditions. Both removing the main stalk and harvesting the side shoots is much more labor intensive than broccoli production. Baby broccoli is also intolerant of temperature extremes and more sensitive to cold temperatures than broccoli. Baby broccoli is grown year round in California and Arizona. Like broccoli, baby broccoli is a good source of vitamin C, vitamin A, folate, iron and potassium, and can be eaten a variety of ways, including raw and cooked.

Therefore, developing new and improved baby broccoli plants having unique characteristics, such as purple stem color, more tender texture and early production, is highly desirable.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there are provided novel purple baby broccoli plants. This invention thus relates to the seeds of purple baby broccoli plants, to the plants of purple baby broccoli plants, and to methods for producing a purple baby broccoli plant containing in its genetic background Brassica oleracea var. italica (broccoli) and Brassica oleracea var. alboglabra (gai-lan), to methods for producing purple baby broccoli plants containing in its genetic material one or more transgenes, and to the transgenic purple baby broccoli plants produced by that method.

In another aspect, the present invention provides for methods of producing a purple baby broccoli plant, said method comprising:
a. Crossing a broccoli plant with a gai-lan plant to produce an $F_1$ broccoli×gai-lan hybrid plant;
b. Crossing said $F_1$ broccoli×gai-lan hybrid plant with a Brassica oleracea plant having purple head and purple stems to produce further $F_1$ plants;
c. Selecting further $F_1$ plants having purple head and purple stem color to produce a broccoli×gai-lan parent plant having purple head and purple stem color;
d. Crossing a broccoli plant and a purple head broccoli plant to produce a broccoli parent plant having a purple head with a long floret stem;
e. Crossing said broccoli×gai-lan parent plant having purple head and purple stem color with said broccoli parent plant having purple head with long floret stem to produce a purple baby broccoli plant.

In another aspect of the invention, the method further comprises selection for a high number of side shoots.

In another aspect of the invention, the method further comprises one or more backcrosses of said further $F_1$ plants to said $F_1$ broccoli×gai-lan hybrid plant or sib-crosses to produce resultant plants. In another aspect, the method further comprises selecting said resultant plants based on purple color to produce a broccoli×gai-lan parent plant having purple head and purple stem color. In another aspect, the method further comprises selection for a high number of side shoots.

The invention further provides methods for developing purple baby broccoli plants in a broccoli plant breeding program using plant breeding techniques including recurrent selection, backcrossing, pedigree breeding, restriction fragment length polymorphism enhanced selection, genetic marker enhanced selection, and transformation. Seeds, purple baby broccoli plants, and parts thereof, produced by such breeding methods are also part of the invention.

In another aspect, the invention relates to $F_1$ hybrid purple baby broccoli plants, including but not limited to K1-703 and K4-706. This invention thus relates to the seeds of purple baby broccoli K1-703 and K4-706, to the plants of purple baby broccoli K1-703 and K4-706, and to methods for producing a purple baby broccoli plant produced by crossing purple baby broccoli K1-703 or K4-706 with itself or another broccoli plant, to methods for producing purple baby broccoli K1-703 or K4-706 containing in its genetic material one or more transgenes, and to the transgenic purple baby broccoli plants produced by that method.

In another aspect, the present invention provides regenerable cells for use in tissue culture of purple baby broccoli plants. In a further aspect, the present invention provides regenerable cells for use in tissue culture of purple baby broccoli plants, including but not limited to K1-703 and K4-706. The tissue culture will preferably be capable of regenerating plants having essentially all of the physiological and morphological characteristics of the foregoing broccoli plant, and of regenerating plants having substantially the same genotype as the foregoing broccoli plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides broccoli plants regenerated from the tissue cultures of the invention.

Another aspect of the invention is to provide methods for producing other purple baby broccoli plants derived from purple baby broccoli plants, including but not limited to K1-703 and K4-706. Purple baby broccoli plants derived by the use of those methods are also part of the invention.

In another aspect, the present invention provides for single gene converted plants and locus conversion plants of purple baby broccoli plants. In a further aspect, the present invention provides for single gene converted plants and locus conversion plants of purple baby broccoli plants, including but not limited to K1-703 and K4-706. The single transferred gene may preferably be a dominant or recessive allele. Preferably, the single transferred gene or locus conversion will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring broccoli gene or a transgene introduced through genetic engineering techniques.

In another aspect, the present invention provides for the parent lines of purple baby broccoli plants, including but not limited to Brassica oleracea lines CMS AS001P, AS001P, CMS AS002P and AS002P. This invention thus relates to the seeds of lines CMS AS001P, AS001P, CMS AS002P and AS002P, to the plants of lines CMS AS001P, AS001P, CMS AS002P and AS002P, and to methods for producing a purple baby broccoli plant produced by crossing lines CMS AS001P, AS001P, CMS AS002P and AS002P, to methods for producing lines CMS AS001P, AS001P, CMS AS002P and AS002P containing in their genetic material one or more transgenes, and to the plants produced by that method.

In another aspect, the present invention provides regenerable cells for use in tissue culture of parent lines CMS AS001P, AS001P, CMS AS002P and AS002P. The tissue culture will preferably be capable of regenerating plants having essentially all of the physiological and morphological characteristics of the foregoing broccoli plant, and of regenerating plants having substantially the same genotype as the foregoing broccoli plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides broccoli plants regenerated from the tissue cultures of the invention.

Another aspect of the invention is to provide methods for producing other purple baby broccoli plants derived from parent lines CMS AS001P, AS001P, CMS AS002P and AS002P. Purple baby broccoli plants derived by the use of those methods are also part of the invention.

In another aspect, the present invention provides for single gene converted plants and locus conversion plants of parent *Brassica oleracea* lines CMS AS001P, AS001P, CMS AS002P and AS002P. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring broccoli gene introduced via backcrossing or a transgene introduced through genetic engineering techniques.

The purple baby broccoli plants and parent lines CMS AS001P, AS001P, CMS AS002P and AS002P of this invention may further comprise, or have, a cytoplasmic factor or other factor that is capable of conferring male sterility. Male sterility may also be provided by nuclear genes such as the recessive ms gene. Parts of the broccoli plants of the present invention are also provided, such as pollen obtained from an inbred plant and an ovule of the inbred plant.

In a further aspect of the invention, the genetic complement of purple baby broccoli plants, including but not limited to K1-703 and K4-706, and/or *Brassica oleracea* lines CMS AS001P, AS001P, CMS AS002P and AS002P is provided. The phrase 'genetic complement' is used to refer to the aggregate of nucleotide sequences, the expression of which sequences defines the phenotype of a cell or tissue of that plant. A genetic complement thus represents the genetic makeup of a cell, tissue or plant, and a hybrid genetic complement represents the genetic makeup of a hybrid cell, tissue or plant. The invention thus provides *Brassica oleracea* plant cells that have a genetic complement in accordance with the *Brassica oleracea* plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that purple baby broccoli K1-703 and K4-706, and/or *Brassica oleracea* lines CMS AS001P, AS001P, CMS AS002P and AS002P could be identified by any of the many well-known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858), and Single Nucleotide Polymorphisms (SNPs) (Wang et al., 1998).

In yet another aspect, the present invention provides hybrid genetic complements, as represented by *Brassica oleracea* plant cells, tissues, plants, and seeds, formed by the combination of a haploid genetic complement of a *Brassica oleracea* plant of the invention with a haploid genetic complement of a second *Brassica oleracea* plant, preferably, another distinct *Brassica oleracea* plant. In another aspect, the present invention provides a *Brassica oleracea* plant regenerated from a tissue culture that comprises a hybrid genetic complement of this invention.

In another aspect, the invention provides a method of determining the genotype of a plant of purple baby broccoli plants, including but not limited to K1-703 or K4-706, and/or *Brassica oleracea* lines CMS AS001P, AS001P, CMS AS002P and AS002P comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In addition to the exemplary aspects and embodiments described above, further aspects and embodiments will become apparent by reference by study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. The "allele" is any of one or more alternative forms of a gene, all of which relate to one trait or characteristic. In a diploid cell or organism, the two alleles of a given gene occupy corresponding loci on a pair of homologous chromosomes.

Baby broccoli. Baby broccoli is a hybrid of broccoli (*Brassica oleracea* L. var. *italica*) and gai-lan (*Brassica oleracea* var. *alboglabra*), also known as kai-lan, Chinese broccoli, and Chinese kale. Baby broccoli is a green vegetable similar to broccoli, but with smaller florets, longer thinner tender stalks, and a subtle sweet flavor with a peppery taste. It resembles a broccoli raab with an asparagus stem. Baby broccoli is known by the trade names Broccolini® and Aspabroc, as well as Asparation®, asparations, Bimi®, broccoletti, broccolette and Tenderstem™.

Backcrossing. "Backcrossing" is a process in which a breeder repeatedly crosses hybrid progeny back to one of the parents, for example, a first generation hybrid $F_1$ with one of the parental genotype of the $F_1$ hybrid. Backcrossing can be used to introduce one or more single locus conversions from one genetic background into another.

Broccoli. A member of the Brassicaceae family that is classified in the *Italica* cultivar group of the species *Brassica oleracea* and has a chromosome number of 2n=18.

CMS. Cytoplasmic male sterile.

Crossing. The mating of two parent plants.

Cross-pollination. Fertilization by the union of two gametes from different plants.

Curd. A collection of florets in a single floral structure. Also called "head".

Diploid. A cell or organism having two sets of chromosomes. The total number of chromosomes in diploid cells is described as 2n, which is twice the number of chromosomes in a haploid cell (n).

Emasculate. The removal of plant male sex organs or the inactivation of the organs with a cytoplasmic or nuclear genetic factor or a chemical agent conferring male sterility.

Essentially all the physiological and morphological characteristics. A plant having essentially all the physiological and morphological characteristics means a plant having the physiological and morphological characteristics of the recurrent parent, except for the characteristics derived from the converted gene.

$F_1$ hybrid. The first generation progeny of the cross of two nonisogenic plants.

Floret. The flower bud cluster including that part of the secondary stem supporting the flower bud cluster, which collectively make up the curd or head.

Floret stem. The floret stem is the stem supporting the flower bud cluster. It is not limited to the secondary stem, but also tertiary stems and others.

Gai-lan. *Brassica oleracea* var. *alboglabra*, also known as kai-lan, Chinese broccoli, or Chinese kale. Gai-lan is a leaf vegetable having thick, flat, glossy blue-green leaves with thick stems and a small number of tiny flower heads.

Gene. As used herein, "gene" refers to a segment of nucleic acid. A gene can be introduced into a genome of a species, whether from a different species or from the same species, using transformation or various breeding methods.

Gene converted (conversion). "Gene converted" or "Single gene converted" (or conversion) plant refers to plants which are developed by a plant breeding technique called backcrossing wherein essentially all of the desired morphological and physiological characteristics of an inbred are recovered in addition to the one or more genes transferred into the inbred via the backcrossing technique or via genetic engineering.

Genotype. The genetic constitution of a cell or organism.

Haploid. A cell or organism having one set of the two sets of chromosomes in a diploid.

Head. A collection of florets in a single floral structure. Also called "curd".

Linkage. Refers to a phenomenon wherein alleles on the same chromosome tend to segregate together more often than expected by chance if their transmission was independent.

Locus. A defined segment of DNA.

Locus conversion (also called a 'trait conversion'). A locus conversion refers to plants that have been modified in a manner that retains the overall genetics of the plant and further comprises one or more loci with a specific desired trait, such as male sterility, insect control, disease control or herbicide tolerance. Examples of single locus conversions include mutant genes, transgenes and native traits finely mapped to a single locus. One or more locus conversion traits may be introduced into a single plant.

Long floret stem. As used herein, a long floret stem is at least 6.0 cm in length.

Pedigree breeding/selection. "Pedigree breeding" is a breeding method used during the inbreeding of populations of self- and cross-pollinated species for the development of desirable homogeneous lines. Pedigree selection generally begins with an $F_2$ population and continues until homogeneous lines are developed.

Petiole. "Petiole" means the stalk of a leaf, attaching the leaf blade to the stem.

Phenotype. The detectable characteristics of a cell or organism, which characteristics are the manifestation of gene expression.

Plant. "Plant" includes plant cells, plant protoplasts, plant ovules, plant cells of tissue culture from which *B. oleracea* plants can be regenerated, plant calli, plant clumps and plant cells that are intact in plants, or parts of plants such as pollen, flowers, seeds, leaves, stems, and the like.

Purple baby broccoli. Purple baby broccoli is a hybrid of broccoli (*Brassica oleracea* L. var. *italica*) and gai-lan (*Brassica oleracea* var. *alboglabra*), also known as Chinese broccoli, Chinese kale, or kailaan, as described herein, and differs from baby broccoli and traditional purple sprouting broccoli by having improved purple stem color, more tender texture and early maturity. Representative purple baby broccoli plants described herein include, but are not limited to, K1-703, K4-706, 12KA075sis, 12KA077 and 12KA069.

Purple head. A purple head includes, but is not limited to, the following color designations from the RHS color chart: RHS N187A, 79A, N79A, and N92A.

Purple stems. Purple stems include, but are not limited to, the following color designations from the RHS color chart: RHS N187A, N77C, N79A, and N79C.

Quantitative Trait Loci. "Quantitative Trait Loci" (QTL) refers to genetic loci that control to some degree, numerically representable traits that are usually continuously distributed.

Regeneration. "Regeneration" refers to the development of a plant from tissue culture.

RHS. "RHS" refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Self-pollination. The transfer of pollen from the anther to the stigma of the same plant.

Sib-cross. The cross of two plants having common parentage.

Side shoots. Axillary stems except for a main stem, and supporting and forming part of individual florets.

Single gene converted. "Single gene converted" or "conversion plant" refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Tissue culture. A composition comprising isolated cells of the same or a different type of collection of such cells organized into parts of a plant.

Transgene. A genetic locus comprising a sequence which has been introduced into the genome of a plant by transformation.

The following detailed description is of the currently contemplated modes of carrying out the invention. The description is not to be taken in a limiting sense, but is made merely for the purpose of illustrating the general principles of the invention, since the scope of the invention is best defined by the appended claims.

The present invention is directed to purple baby broccoli plants and seeds, the parents thereof, and methods of producing purple baby broccoli plants. Purple baby broccoli is a novel plant type distinguished from baby broccoli by unexpectedly having very dark purple color on the stems and florets, very early maturity, very uniform head maturity, and head spears that are smoother with fewer leaves. Purple baby broccoli is phenotypically distinguished from traditional purple sprouting broccoli by having improved darker purple stem color, longer and more tender and milder tasting stems, more detached florets instead of one broccoli head or loose broccoli head, and earlier maturity. In trials, purple baby broccoli was more uniformly purple than the most similar comparison varieties. To date, there are no known purple baby broccoli varieties other than the present invention, and thus, purple baby broccoli is different from known varieties of broccoli, including baby broccoli. The closest known product to purple baby broccoli is a variety called Purple Peacock, which is a broccoli-kale (*Brassica oleracea* var. *acephala*) cross, but has leaves that are very fringy like Red Russian or Red Winter kale. Purple baby broccoli contains in its genetic background *Brassica oleracea* var. *italica* (broccoli) and *Brassica oleracea* var. *alboglabra* (gai-lan).

The present invention is further directed to methods of producing purple baby broccoli plants and seeds, to the purple baby broccoli plants and seeds produced by the method, and to the parent lines used to produce the purple baby broccoli. Therefore, any methods using purple baby broccoli are part of this invention: selfing, backcrosses, hybrid breeding, and crosses to populations.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Further Embodiments of the Invention

Broccoli, and *Brassica oleracea* in general, is an important and valuable vegetable crop. Thus, a continuing goal of broccoli plant breeders is to develop stable, high yielding broccoli cultivars and hybrids that are agronomically sound. To accomplish this goal, the broccoli breeder must select and develop broccoli plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of broccoli plant breeding is to develop new, unique, and superior broccoli cultivars and hybrids. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same broccoli traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior broccoli cultivars.

The development of commercial broccoli cultivars requires the development of broccoli varieties, the crossing of these varieties and selection of superior hybrid crosses. The hybrid seed is produced by manual crosses between selected male-fertile parents or by using male sterility systems. These hybrids are selected for certain single gene traits such as fruit color, flower color, pubescence color or herbicide resistance which indicate that the seed is truly a hybrid. Additional data on parental lines, as well as the phenotype of the hybrid, influence the breeder's decision whether to continue with the specific hybrid cross.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In a multiple-seed procedure, broccoli breeders commonly harvest two or more seeds from each plant in a population and bulk them to form a bulk sample. Part of the bulk is used to plant the next generation and part is put in reserve. The procedure has been referred to as modified single-seed descent or the "pod-bulk" (for bean crops) technique.

The multiple-seed procedure has been used to save labor at harvest. It is considerably faster to extract seeds with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into broccoli varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed broccoli plants using transformation methods as described below to incorporate transgenes into the genetic material of the broccoli plant(s).

Expression Vectors for Broccoli Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.*, 5:387 (1987); Teeri, et al., *EMBO J.*, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Broccoli Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in broccoli. Optionally, the inducible promoter is operably linked to a nucleotide sequence encoding a signal sequence which is operably linked to a gene for expression in broccoli. With an inducible promoter, the rate of transcription increases in response to an inducing agent.

Any inducible promoter can be used in the instant invention. See Ward, et al., *Plant Mol. Biol.,* 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genet.,* 227:229-237 (1991) and Gatz, et al., *Mol. Gen. Genet.,* 243:32-38 (1994)) or Tet repressor from Tn10 (Gatz, et al., *Mol. Gen. Genet.,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS,* 88:0421 (1991).

B. Constitutive Promoters:

A constitutive promoter is operably linked to a gene for expression in broccoli or the constitutive promoter is operably linked to a nucleotide sequence encoding a signal sequence which is operably linked to a gene for expression in broccoli.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT Application No. WO 96/30530.

C. Tissue-Specific or Tissue-Preferred Promoters:

A tissue-specific promoter is operably linked to a gene for expression in broccoli. Optionally, the tissue-specific promoter is operably linked to a nucleotide sequence encoding a signal sequence which is operably linked to a gene for expression in broccoli. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is broccoli. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes That Confer Resistance to Pests or Disease and That Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (Arabidopsis RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., *Plant Mol. Biol.*, 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of *Streptomyces nitrosporeus* α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266, 317 to Tomalski, et al., who disclose genes encoding insect-specific, paralytic neurotoxins.

8. An insect-specific venom produced in nature, by a snake, a wasp, etc. For example, see Pang, et al., Gene, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.*, 23:691 (1993), who teach the nucleotide sequence of a cDNA encoding tobacco hornworm chitinase, and Kawalleck, et al., *Plant Mol. Biol.*, 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.,* 89:43 (1993), of heterologous expression of a cecropin-β, lytic peptide analog to render transgenic tobacco plants resistant to *Pseudomonas solanacearum.*

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.,* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., *Nature,* 366:469 (1993), who show that transgenic plants expressing recombinant antibody genes are protected from virus attack.

17. A developmental-arrestive protein produced in nature by a pathogen or a parasite. Thus, fungal endo-α-1, 4-D-polygalacturonases facilitate fungal colonization and plant nutrient released by solubilizing plant cell wall homo-α-1, 4-D-galacturonase. See Lamb, et al., *Bio/technology,* 10:1436 (1992). The cloning and characterization of a gene which encodes a bean endopolygalacturonase-inhibiting protein is described by Toubart, et al., *Plant J.,* 2:367 (1992).

18. A developmental-arrestive protein produced in nature by a plant. For example, Logemann, et al., *Bio/technology,* 10:305 (1992), have shown that transgenic plants expressing the barley ribosome-inactivating gene have an increased resistance to fungal disease.

19. Genes involved in the Systemic Acquired Resistance (SAR) Response and/or the pathogenesis-related genes. Briggs, S., *Current Biology,* 5(2) (1995).

20. Antifungal genes. See Cornelissen and Melchers, *Plant Physiol.,* 101:709-712 (1993); Parijs et al., *Planta* 183:258-264 (1991) and Bushnell et al., *Can. J. of Plant Path.* 20(2):137-149 (1998).

21. Genes that confer resistance to *Phytophthora* root rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al., *Phytophthora* Root Rot Resistance Gene Mapping in Soybean, Plant Genome IV Conference, San Diego, Calif. (1995).

Any of the above listed disease or pest resistance genes (1-21) can be introduced into the claimed broccoli cultivar through a variety of means including but not limited to transformation and crossing.

B. Genes That Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988) and Miki, et al., *Theor. Appl. Genet.,* 80:449 (1990), respectively.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research,* 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology,* 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.,* 83:435 (1992).

3. An herbicide that inhibits photosynthesis, such as a triazine (psbA and gs+ genes) and a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).

4. Acetohydroxy acid synthase, which has been found to make plants that express this enzyme resistant to multiple types of herbicides, has been introduced into a variety of plants. See Hattori, et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.,* 106:17 (1994)), genes for glutathione reductase and superoxide dismutase (Aono, et al., *Plant Cell Physiol.,* 36:1687 (1995)), and genes for various phosphotransferases (Datta, et al., *Plant Mol. Biol.,* 20:619 (1992)).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282, 837, 5,767,373, and International Publication WO 01/12825.

Any of the above listed herbicide genes (1-5) can be introduced into the claimed broccoli cultivar through a variety of means including, but not limited to, transformation and crossing.

C. Genes That Confer or Contribute to a Value-Added Trait, such as:

1. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

2. Decreased phytate content—1) Introduction of a phytase-encoding gene enhances breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. See Raboy et al., *Maydica* 35:383 (1990).

3. Increased sweetness of the broccoli by introducing a gene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense gene of stearyl-ACP desaturase to increase stearic acid content of the plant. See Knultzon, et al., *PNAS*, 89:2625 (1992).

5. Modified carbohydrate composition effected, for example, by introducing into plants a gene coding for an enzyme that alters the branching pattern of starch. See Shiroza, et al., *J. Bacteriol.*, 170:810 (1988) (nucleotide sequence of *Streptococcus* mutants fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus lichenifonnis* α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

6. Elevated oleic acid via FAD-2 gene modification and/or decreased linolenic acid via FAD-3 gene modification. See U.S. Pat. Nos. 6,063,947; 6,323,392; and PCT Publication WO 93/11245.

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.*, 19:611-622 (1992).

Methods for Broccoli Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227:1229 (1985); Curtis, et al., *Journal of Experimental Botany*, 45:279, 1441-1449 (1994); Tones, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.*, 12 (3, January), 165-169 (1993); Aragao, F. J. L., et al., *Plant Mol. Biol.*, 20 (2, October), 357-359 (1992); Aragao, F. J. L., et al., *Plant Cell Rep.*, 12 (9, July), 483-490 (1993); Aragao, *Theor. Appl. Genet.*, 93:142-150 (1996); Kim, J., Minamikawa, T., *Plant Sci.*, 117:131-138 (1996); Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast SWD8732 have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$) precipitation, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Saker, M., Kuhne, T., *Biologia Plantarum*, 40(4): 507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Following transformation of broccoli target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic broccoli, such as a new transgenic purple baby broccoli. Alternatively, a genetic trait which has been engineered into a particular broccoli cultivar using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "*Brassica oleracea* plant" or "broccoli plant" or "purple baby broccoli plant" is used in the context of the present invention, this also includes any gene conversions of that variety. The term "gene converted plant" as used herein refers to those broccoli or purple baby broccoli plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental broccoli plant which contributes the gene for the desired characteristic is termed the "nonrecurrent" or "donor parent." This terminology refers to the fact that the nonrecurrent parent is used one time in the backcross protocol and therefore does not recur. The parental broccoli plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a purple baby broccoli plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics, of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948, 957, and 5,969,212, the disclosures of which are specifically hereby incorporated by reference.

Locus Conversions of Purple Baby Broccoli, AS001P, CMS AS001P, AS002P, CMS AS002P, K1-703 and K4-706

Purple baby broccoli plants, including but not limited to K1-703 and K4-706, and *Brassica oleracea* lines AS001P, CMS AS001P, AS002P, and CMS AS002P represent new base genetic varieties into which a new locus may be introgressed. Direct transformation and backcrossing represent two important methods that can be used to accomplish such an introgression. The term locus conversion is used to designate the product of such an introgression. A locus conversion of purple baby broccoli and *Brassica oleracea* plants, including but not limited to K1-703 and K4-706, and lines AS001P, CMS AS001P, AS002P, and CMS AS002P will retain the genetic integrity of purple baby broccoli, including but not limited to K1-703 and K4-706, and lines AS001P, CMS AS001P, AS002P, and CMS AS002P and will comprise at least 90%, 91%, 92%, 93%, 94%, 95%, 96%, 97%, 98% or 99% of the genetic identity of purple baby broccoli plants, including but not limited to K1-703 and K4-706, and lines AS001P, CMS AS001P, AS002P, and CMS AS002P as determined by using SSR markers or SNP markers. A locus conversion can be a native trait or a transgenic trait.

Tissue Culture

Further reproduction of the variety can occur by tissue culture and regeneration. Tissue culture of various tissues of broccoli and regeneration of plants therefrom is well known and widely published. For example, reference may be had to Kumar, P., "Clonal Propagation in Broccoli (*Brassica oleracea* L. var. *italica*): Plant Tissue Culture,", Lambert Academic Publishing (2012); Anderson et al., *J. Amer. Soc. Hort. Sci.*, 102:69-73 (1977); Kim, et al., *J. Plant Biology*, 45(3):177-181 (2002); Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce purple baby broccoli plants.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a purple baby broccoli plant by crossing a first parent Brassica oleracea plant with a second parent Brassica oleracea plant wherein the first or second parent Brassica oleracea plant is a plant of Brassica oleracea lines CMS AS001P, AS001P, CMS AS002P and AS002P or purple baby broccoli. Thus, any such methods using Brassica oleracea lines CMS AS001P, AS001P, CMS AS002P and AS002P or purple baby broccoli are part of this invention: selfing, backcrosses, hybrid production, crosses to populations, and the like. All plants produced using Brassica oleracea lines CMS AS001P, AS001P, CMS AS002P and AS002P or purple baby broccoli as at least one parent are within the scope of this invention, including those developed from cultivars derived from Brassica oleracea lines CMS AS001P, AS001P, CMS AS002P and AS002P or purple baby broccoli. Advantageously, these broccoli could be used in crosses with other, different, broccoli plants to produce the first generation ($F_1$) broccoli hybrid seeds and plants with superior characteristics. The plants of the invention can also be used for transformation where exogenous genes are introduced and expressed by the cultivar of the invention. Genetic variants created either through traditional breeding methods using Brassica oleracea lines CMS AS001P, AS001P, CMS AS002P and AS002P or purple baby broccoli or through transformation of Brassica oleracea lines CMS AS001P, AS001P, CMS AS002P and AS002P or purple baby broccoli by any of a number of protocols known to those of skill in the art are intended to be within the scope of this invention.

The following describes breeding methods that may be used with Brassica oleracea lines CMS AS001P, AS001P, CMS AS002P and AS002P or purple baby broccoli in the development of further broccoli plants. One such embodiment is a method for developing Brassica oleracea lines CMS AS001P, AS001P, CMS AS002P and AS002P or purple baby broccoli progeny Brassica oleracea plants in a Brassica oleracea plant breeding program comprising: obtaining the Brassica oleracea plant, or a part thereof, of Brassica oleracea lines CMS AS001P, AS001P, CMS AS002P and AS002P or purple baby broccoli, utilizing said plant or plant part as a source of breeding material, and selecting a Brassica oleracea line progeny plant with molecular markers in common with Brassica oleracea lines CMS AS001P, AS001P, CMS AS002P and AS002P or purple baby broccoli. Breeding steps that may be used in the Brassica oleracea plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of Brassica oleracea lines CMS AS001P, AS001P, CMS AS002P and AS002P or purple baby broccoli progeny broccoli plants, comprising crossing Brassica oleracea lines CMS AS001P, AS001P, CMS AS002P and AS002P or purple baby broccoli with another broccoli plant, thereby producing a population of broccoli plants, which, on average, derive 50% of their alleles from Brassica oleracea lines CMS AS001P, AS001P, CMS AS002P and AS002P or purple baby broccoli. A plant of this population may be selected and repeatedly selfed or sibbed with a broccoli cultivar resulting from these successive filial generations. One embodiment of this invention is the broccoli cultivar produced by this method and that has obtained at least 50% of its alleles from Brassica oleracea lines CMS AS001P, AS001P, CMS AS002P and AS002P or purple baby broccoli.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus the invention includes Brassica oleracea lines CMS AS001P, AS001P, CMS AS002P and AS002P or purple baby broccoli progeny plants comprising a combination of at least two Brassica oleracea lines CMS AS001P, AS001P, CMS AS002P and AS002P or purple baby broccoli traits, so that said progeny plant is not significantly different for said traits than Brassica oleracea lines CMS AS001P, AS001P, CMS AS002P and AS002P or purple baby broccoli as determined at the 5% significance level when grown in the same environmental conditions. Using techniques described herein, molecular markers may be used to identify said progeny plant as a Brassica oleracea line CMS AS001P, AS001P, CMS AS002P or AS002P or purple baby broccoli progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of Brassica oleracea lines CMS AS001P, AS001P, CMS AS002P and AS002P or purple baby broccoli may also be characterized through their filial relationship with lines CMS AS001P, CMS AS002P and AS002P or purple baby broccoli, as for example, being within a certain number of breeding crosses of lines CMS AS001P, AS001P, CMS AS002P and AS002P or purple baby broccoli. A breeding cross is a cross made to introduce new genetics into the progeny, and is distinguished from a cross, such as a self or a sib cross, made to select among existing genetic alleles. The lower the number of breeding crosses in the pedigree, the closer the relationship between lines CMS AS001P, AS001P, CMS AS002P and AS002P or purple baby broccoli and its progeny. For example, progeny produced by the methods described herein may be within 1, 2, 3, 4, or 5 breeding crosses of lines CMS AS001P, AS001P, CMS AS002P and AS002P or purple baby broccoli.

As used herein, the term "plant" includes plant cells, plant protoplasts, plant cell tissue cultures from which broccoli plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

EXAMPLES

Example 1. Development of Parental Lines AS001P and CMS AS001P

In 2000, an $F_1$ was made from a cross between broccoli line 194-6-2 and Broccoli OP Purple. 194-6-2 is a doubled haploid broccoli line bred by using common broccoli and gai-lan. 194-6-2 is the parent of Asparation® baby broccoli, which is green in color and has many side stems with excellent texture. Broccoli OP Purple is a selected line from European traditional OP broccoli variety which has good purple color on its stem. In 2001, $F_2$ population and backcross population to 194-6-2 were made. In 2002, selected plants from the $F_2$ population and the backcross population were crossed respectively. Further two times back-crossed to 194-6-2 and two times sib-cross were added to this population to improve its purple color, number of side shoots and texture. In 2010, the line which has purple color, many side shoots and good texture was obtained and the line was named as AS001P for maintainer and CMS AS001P for CMS type. CMS AS001P is used as the female parent for purple baby broccoli K1-703 and 12KA069, and AS001P is used as the male parent for purple baby broccoli K4-706.

Example 2. Development of Parental Lines AS002P and CMS AS002P

In 2004, an $F_1$ was made from a cross between H669 and No47388. H669 is common broccoli and the parent of Asparation® baby broccoli. No47388 is an $F_3$ line of a purple single head broccoli in Sakata. In 2005, sib-cross was made between selected plants. In 2010, the broccoli line which has purple, single head with a long floret stem was obtained, and this line was named AS002P. AS002P is used as the male parent for purple baby broccoli K1-703 and 12KA077. CMS AS002P is the cytoplasmic male sterile version of AS002P and is used as the female parent of purple baby broccoli K4-706.

Example 3. Creation of Purple Baby Broccoli K1-703

In 2011, an $F_1$ test cross was made between lines CMS AS001P and AS002P, and the $F_1$ purple baby broccoli was named K1-703. From 2012, trials had been conducted in Japan, UK and US. Purple baby broccoli K1-703 has better purple color on its stem, much more tender texture and much earlier maturity than other baby broccoli or traditional purple sprouting broccoli varieties.

Example 4. Method for Producing Purple Baby Broccoli

A method for producing a purple baby broccoli plant, said method comprising:
a. Crossing a broccoli plant with a gai-lan plant to produce an $F_1$ broccoli×gai-lan hybrid plant;

b. Crossing said $F_1$ broccoli×gai-lan hybrid plant with a *Brassica oleracea* plant having purple head and purple stems to produce further $F_1$ plants;
c. Selecting further $F_1$ plants having purple head and purple stem color to produce a broccoli×gai-lan parent plant having purple head and purple stem color;
d. Crossing a broccoli plant and a purple head broccoli plant to produce a broccoli parent plant having a purple head with a long floret stem;
e. Crossing said broccoli×gai-lan parent plant having purple head and purple stem color with said broccoli parent plant having purple head with long floret stem to produce a purple baby broccoli plant.

In another aspect, the method further comprises selection for plants having a high number of side shoots.

In another aspect, the method further comprises one or more backcrosses of said further $F_1$ plants to said $F_1$ broccoli×gai-lan hybrid plant or sib-crosses to produce resultant plants. In another aspect, the method further comprises selecting said resultant plants based on purple color to produce a broccoli×gai-lan parent plant having purple head and purple stem color. In another aspect, the method further comprises selection for plants having a high number of side shoots.

Although the above Examples 1 and 2 describe some particular broccoli lines used in the method for producing purple baby broccoli, the lines described are examples and the method is not limited to those particular lines. Any broccoli, gai-lan, *Brassica oleracea* plant having purple head and purple stems, or purple head broccoli may be used in the method to produce purple baby broccoli.

Example 5. Creation of Additional Purple Baby Broccoli Plants

Representative purple baby broccoli plants described herein were produced by the method of the present invention and include, but are not limited to, K1-703, K4-706, 12KA075sis, 12KA077 and 12KA069. Purple baby broccoli K4-706 was produced by crossing parent lines CMS AS002P×AS001P. Purple baby broccoli 12KA075sis was produced by crossing parent plants BoBopBl./BoBop-Bl.Bo.-sib-1-2-2-3-1-1×Bo47388Sib.Bo./Bo47388Sib.Bo.-3-sib-2-2. Purple baby broccoli 12KA077 was produced by crossing parent plants BoBopBl./BoBopBl.Bo.-sib-1-2-2-3-1-1×AS002P. Purple baby broccoli 12KA069 was produced by crossing parent plants CMS AS001P×BoBopBl./669 47388Sib.-1-3.

Tables

Tables 1-2 show the results of trials planted in 2013 and 2014 in Salinas, Calif. comparing the phenotypic and morphological characteristics of hybrid purple baby broccoli plants (K1-703, 12KA075sis, 12KA077, 12KA069, and K4-706), parental lines (194-6-2CMS (U.S. Pat. No. 6,274, 793), CMS AS001P, AS001P, AS002P, CMS H669, H669, 194-6-2), and similar commercial broccoli varieties (Aspabroc (baby broccoli), Santee, Purple Peacock, Summer Purple Sprouting). In Table 1, the trial was sown on Mar. 27, 2013 and transplant was Apr. 29, 2013, and in Tables 2A and 2B, the trial was sown on May 5, 2014 and transplant was Jun. 10, 2014. In the Tables, 'NA' indicates data not available.

TABLE 1

| | | Variety | | | | | | |
|---|---|---|---|---|---|---|---|---|
| | | K1-703 (Purple baby broccoli) | CMS AS001P | 194-6-2CMS | Aspabroc (baby broccoli) | Santee | Purple Peacock | Summer Purple Sprouting |
| Region of Adaptation | | | | | | | | |
| 1 = Northwest 2 = North Central 3 = Northeast 4 = Southeast 5 = Southwest 6 = Most Regions 7 = Pacific Coast 8 = Other | | 6 | 6 | 6 | 6 | 6 | 6 | 6 |
| Location and year of Data Collection | | Salinas 2013 | Salinas 2013 | Salinas 2013 | Salinas 2013 | Salinas 2013 | Salinas 2013 | Salinas 2013 |
| Species | Species name | *B. oleracea* | *B. oleracea* | *B. oleracea* | *B. oleracea* | *B. oleracea* | *B. oleracea* | *B. oleracea* |
| Maturity | | | | | | | | |
| Harvest Season | 1 = Fall 2 = Fall/Winter 3 Winter/Spring 4 = Spring/Summer 5 = Summer 6 = Summer/Fall | 4 | 4 | 4 | 4 | 4 | 4 | 4 |
| Spring Planted | Days from Direct Seeding to 50% Harvest | 85 | 80 | 80 | 80 | 110 | 90 | 105 |
| | Days from Transplanting to 50% Harvest | 55 | 50 | 50 | 50 | 75 | 60 | 65 |
| | Length of Harvest Period in days | 10 | 10 | 10 | 10 | 30 | 20 | 10 |
| Time of beginning of flowering | 1 = Early 2 = Medium-Early 3 = Medium 4 = Medium-Late 5 = Late | 2 | 1 | 1 | 1 | 5 | 3 | 4 |
| Plant (At Harvest) | | | | | | | | |
| Plant Height (from soil line to top of leaves) | cm | 60.0 | 50.8 | 52.0 | 60.0 | 60.0 | 45.0 | 75.0 |
| Head Height (from soil line to top of head) | cm | 40.0 | 42.0 | 50.8 | 49.0 | 70.0 | 30.0 | 50.0 |
| Plant Branches | 1 = Few 2 = Medium 3 = Many | 2 | 2 | 2 | 3 | 3 | 2 | 2 |
| Branch Number | Total number of branches | 10 | 20 | 13 | 25 | 50 | 30 | 30 |
| Plant Habit | 1 = Spreading 2 = Intermediate 3 = Compact | 2 | 3 | 3 | 2 | 2 | 3 | 2 |
| Market Class | 1 = Fresh Market 2 = Processing 3 = Both | 1 | 1 | 1 | 1 | 1 | 1 | 1 |
| Life Cycle | 1 = Annual 2 = Biennial 3 = Perennial | 1 | 1 | 1 | 1 | 1 | 1 | 1 |
| Type of Variety | 1 = Inbred 2 = Open-Pollinated 3 = First Generation Hybrid | 3 | 1 | 1 | 3 | 3 | 2 | 2 |
| Stem Number | Total number of stems | 22 | 10 | 20 | 50 | 100 | 18 | 12 |
| Stem Length | cm | 6.0 | 7.0 | 20.0 | 18.0 | 10.0 | 8.0 | 10.0 |
| Stem Diameter | cm | 1.6 | 1.2 | 1.5 | 1.5 | 1.2 | 1.0 | 1.0 |
| Stem Color | Color Chart Name and Color Chart Code | RHS N187A | RHS 148A with slight RHS N79C (anthocyanin) | RHS 146B | RHS 146B | RHS 145A, head stems have both RHS 145A and RHS N187A | RHS N187A | RHS 144A |

TABLE 1-continued

|  |  | Variety | | | | | | |
| --- | --- | --- | --- | --- | --- | --- | --- | --- |
|  |  | K1-703 (Purple baby broccoli) | CMS AS001P | 194-6-2CMS | Aspabroc (baby broccoli) | Santee | Purple Peacock | Summer Purple Sprouting |
| Outer Leaves (At Harvest) |  |  |  |  |  |  |  |  |
| Number of Leaves per Plant |  | 40 | 54 | 50 | 60 | 200 | 40 | 40 |
| Width (at Midpoint of plant including petiole) | cm | 22.0 | 17.8 | 11.4 | 16.0 | 12.0 | 15.0 | 20.0 |
| Length (at midpoint of plant including petiole) | cm | 30.0 | 22.9 | 19.0 | 24.0 | 19.0 | 30.0 | 40.0 |
| Petiole Length | cm | 28.0 | 15.2 | 15.2 | 27.0 | 16.0 | 15.0 | 30.0 |
| Leaf Ratio-Length/Width | 1 = (2:1)<br>2 = (3:1)<br>3 = (4:1)<br>4 = (5:1)<br>5 = (6:1) | 1 | 1 | 1 | 1 | 1 | 1 | 1 |
| Leaf Attachment | 1 = Sessile<br>2 = Petiolate<br>3 = Sessile and Petiolate | 2 | 2 | 2 | 2 | 2 | 2 | 2 |
| Wax Presence | 1 = None<br>2 = Weak<br>3 intermediate<br>4 = Strong | 3 | 4 | 3 | 3 | 3 | 3 | 3 |
| Foliage Color (with wax if present) | 1 = Light Green<br>2 = Medium Green<br>3 = Dark Green<br>4 = Grey-Green<br>5 = Blue-Green<br>6 = Purple-Green | 5 | 6 | 3 | 3 | 2 | 6 | 2 |
| Foliage Color (upper) | Color Chart Name and Color Chart Code | Closest to, but darker than RHS 133A | RHS 139A | RHS 137A | RHS 139A | RHS 139A | RHS 137B with RHS N187A blotches | RHS 139A |
| Foliage Color (lower) | Color Chart Name and Color Chart Code | RHS N138A | RHS 137A | RHS 137B | RHS 137A | RHS 137A | RHS 137C with RHS N187A blotches | RHS N138B |
| Leaf Shape | 1 = Narrow Elliptic<br>2 = Elliptic<br>3 = Broad Elliptic | 3 | 2 | 1 | 2 | 1 | 1 | 3 |
| Leaf Base | 1 = Blunt<br>2 = Pointed | 1 | 1.5 | 1.5 | 1 | 1 | 1 | 1 |
| Leaf Apex | 1 = Blunt<br>2 = Pointed | 1 | 1 | 2 | 1 | 1 | 1 | 1 |
| Leaf Margins | 1 = Straight<br>2 = Slightly Wavy<br>3 = Very Wavy | 3 | 2 | 2.5 | 2 | 3 | 3 | 3 |
| Leaf Veins | 1 = Thin<br>2 = Intermediate<br>3 = Thick | 3 | 2 | 1 | 3 | 1 | 1 | 3 |
| Midrib | 1 = Not Raised<br>2 = Slightly Raised<br>3 = Raised | 3 | 3 | 3 | 3 | 3 | 3 | 3 |
| Blistering | 1 = None<br>2 = Weak<br>3 = Intermediate<br>4 = Strong | 4 | 3 | 3 | 2 | 2 | 4 | 4 |
| Attitude (Leaf Angle from Ground) | 1 = Horizontal (0-15 degrees)<br>3 = Semi-erect (35-55 degrees)<br>5 = Erect (80-100 degrees) | 3 | 5 | 5 | 3 | 4 | 3 | 3 |
| Torsion of Leaf Tip | 1 = None<br>2 = Weak | 4 | 2 | 2 | 3 | 2 | 3 | 4 |

TABLE 1-continued

| | | Variety | | | | | | |
|---|---|---|---|---|---|---|---|---|
| | | K1-703 (Purple baby broccoli) | CMS AS001P | 194-6-2CMS | Aspabroc (baby broccoli) | Santee | Purple Peacock | Summer Purple Sprouting |
| | 3 = Intermediate | | | | | | | |
| | 4 = Strong | | | | | | | |
| Profile of Upper Side of Leaf Head (At Market Maturity) | 1 = Concave<br>2 = Planar<br>3 = Convex | 1 | 2 | 1 | 1.5 | 1 | 2 | 1 |
| Diameter (at widest point) | cm | 14.0 | 10.0 | 6.0 | 15.0 | 11.0 | 17.0 | 11.0 |
| Depth | cm | 16.0 | 10.0 | 8.5 | 18.0 | 22.0 | 20.0 | 13.0 |
| Head Color | 1 = Light Green<br>2 = Medium Green<br>3 = Dark Green<br>4 = Blue-Green<br>5 = Purple<br>6 = Other | 5 | 5 | 2 | 4 | 6 | 6 | 5 |
| Head Color | Color Chart Name and Color Chart Code | RHS N187A and RHS N138A | Closest to but lighter than RHS N187A with RHS 137B | RHS 139B | Closest to RHS N138A | RHS 145A and RHS N187A | Closest to RHS N187A with some RHS 137A | RHS N187A |
| Head Shape | 1 = Circular<br>2 = Transverse Broad Elliptic<br>3 = Transverse Elliptic<br>4 = Transverse Elliptic Narrow | 4 | 4 | 4 | 4 | 1 | 4 | 1 |
| Dome Shape | 1 = Domed<br>2 = Semi-domed<br>3 = Deep Domed | 1 | 1 | 1 | 1 | 1 | 1 | 1 |
| Head Size | 1 = Small<br>2 = Medium<br>3 = Large | 2 | 1 | 2 | 2 | 1 | 2 | 1 |
| Compactness | 1 = Long Pedicels (Loose)<br>2 = Medium<br>3 = Short Pedicels (tight) | 3 | 1 | 1 | 2 | 1 | 2 | 3 |
| Surface Knobbling | 1 = Fine<br>2 = Medium<br>3 = Coarse | 2 | 3 | 3 | 2 | 3 | 3 | 2 |
| Bead Size | 1 = Small<br>2 = Medium<br>3 = Large | 2 | 3 | 3 | 2 | 2 | 2 | 3 |
| Flower Buds | 1 = Even in size<br>2 = Uneven in size (cateye) | 2 | 2 | 1 | 2 | 2 | 2 | 2 |
| Anthocyanin Coloration<br>1 = Absent<br>2 = Present | Leaf Axils | 1 | 1 | 1 | 1 | 1 | 2 | 1 |
| | Leaf Veins | 2 | 2 | 1 | 1 | 1 | 2 | 1 |
| | Leaf Blade | 1 | 1 | 1 | 1 | 1 | 2 | 1 |
| | Entire Plant | 2 | 2 | 1 | 1 | 2 | 2 | 1 |
| | Leaf Petiole | 2 | 2 | 1 | 1 | 1 | 2 | 1 |
| Color of Head Leaves | 1 = White<br>2 = Green<br>3 = Red<br>4 = Purple<br>5 = Other | 5 | 4 | 2 | 2 | 2 | 2 | 2 |
| Color of Head Leaves (upper) | Color Chart Name and Color Chart Code | Closest to but darker than RHS 133A | RHS 139A | RHS 139A | RHS 139A | RHS 139A | RHS 137B | RHS 139A |
| Color of Head Leaves (lower) | Color Chart Name and Color Chart Code | Closest to but darker than RHS N138A | RHS N138C | RHS 137A | RHS 137A | RHS 137A | RHS 137C | RHS N138B |
| Secondary Heads | 1 = Completely absent<br>2 = Basal | 4 | 4 | 4 | 4 | 4 | 2 | 3 |

TABLE 1-continued

|  |  | Variety | | | | | | |
|---|---|---|---|---|---|---|---|---|
|  |  | K1-703 (Purple baby broccoli) | CMS AS001P | 194-6-2CMS | Aspabroc (baby broccoli) | Santee | Purple Peacock | Summer Purple Sprouting |
|  | 3 = Combination<br>4 = Axillary along entire main stem up to main head |  |  |  |  |  |  |  |
| Prominence of Secondary Heads | 1 = Weak<br>2 = Intermediate<br>3 = Strong | 1 | 3 | 3 | 3 | 2 | 1 | 2 |
| Number of Secondary Heads |  | 4 | 9 | 8 | 13 | 12 | 4 | 8 |
| Flower |  |  |  |  |  |  |  |  |
| Flower Color | 1 = White<br>2 = Cream<br>3 = Yellow<br>4 = other | 3 | 3 | 3 | 3 | 3 | 3 | 1 |
| Flower Color | Color Chart Name and Color Chart Code | RHS 10B | RHS 4B | RHS 3B | RHS 4B | RHS 4B | RHS 4B | RHS N155A |
| Flower Stalk Color | 1 = Green<br>2 = Purple<br>3 = Variegated | 2 | 2 | 1 | 1 | 1 | 1 | 1 |
| Flower Stalk Color | Color Chart Name and Color Chart Code | RHS N187A | RHS 148A with slight RHS N79C | RHS 146B | RHS 146B | RHS 143A | RHS 148A with slight RHS N79B | RHS 144A |
| Disease/Insect/Physiological Resistance |  | Unknown | Unknown | Unknown | Unknown | Unknown | Unknown | Unknown |

TABLE 2A

|  |  | Variety | | | | |
|---|---|---|---|---|---|---|
|  |  | K1-703 (Purple baby broccoli) | CMS AS001P | AS001P | AS002P | 12KA075sis (Purple baby broccoli; plot 41530) |
| Region of Adaptation |  |  |  |  |  |  |
| 1 = Northwest 2 = North Central<br>3 = Northeast 4 = Southeast<br>5 = Southwest 6 = Most Regions<br>7 = Pacific Coast 8 = Other |  | 6 | 6 | 6 | 6 | 6 |
| Location and year of Data Collection |  | Salinas 2014 | Salinas 2014 | Salinas 2014 | Salinas 2014 | Salinas 2014 |
| Species | Species name | *B. oleracea* | *B. oleracea* | *B. oleracea* | *B. oleracea* | *B. oleracea* |
| Maturity |  |  |  |  |  |  |
| Harvest Season | 1 = Fall<br>2 = Fall/Winter<br>3 Winter/Spring<br>4 = Spring/Summer<br>5 = Summer<br>6 = Summer/Fall | 5 | 4 | 4 | 4 | 4 |
| Spring Planted | Days from Direct Seeding to 50% Harvest | 85 | 80 | 85 | 90 | 88 |
|  | Days from Transplanting to 50% Harvest | 55 | 50 | 50 | 55 | 53 |
|  | Length of Harvest Period in days | 10 | 10 | 10 | 10 | 10 |
| Time of beginning of flowering | 1 = Early<br>2 = Medium-Early<br>3 = Medium<br>4 = Medium-Late<br>5 = Late | 2 | 1 | 2 | 3 | 3 |

TABLE 2A-continued

| Plant (At Harvest) | | | | | | | |
|---|---|---|---|---|---|---|---|
| Plant Height (from soil line to top of leaves) | cm | | 60.0 | 60.0 | 36.0 | 60.0 | 55.0 |
| Head Height (from soil line to top of head) | cm | | 40.0 | 40.0 | 30.0 | 30.0 | 35.0 |
| Plant Branches | 1 = Few<br>2 = Medium<br>3 = Many | | 2 | 2 | 3 | 1 | 3 |
| Branch Number | Total number of branches | | 22 | 18 | 55 | 20 | 20 |
| Plant Habit | 1 = Spreading<br>2 = Intermediate<br>3 = Compact | | 2 | 3 | 3 | 2 | 2 |
| Market Class | 1 = Fresh Market<br>2 = Processing<br>3 = Both | | 1 | 1 | 1 | 1 | 1 |
| Life Cycle | 1 = Annual<br>2 = Biennial<br>3 = Perennial | | 1 | 1 | 1 | 1 | 1 |
| Type of Variety | 1 = Inbred<br>2 = Open-Pollinated<br>3 = First Generation Hybrid | | 3 | 1 | 1 | 1 | 3 |
| Stem Number | Total number of stems | | 10 | 9 | 9 | 12 | 20 |
| Stem Length | cm | | 6.0 | 8.0 | 7.0 | 8.0 | 12.0 |
| Stem Diameter | cm | | 1.6 | 1.0 | 1.2 | 1.2 | 1.0 |
| Stem Color | Color Chart Name and Color Chart Code | | RHS N187A | RHS 148A with slight RHS N79C (anthocyanin) | RHS 148A with some RHS N79C | RHS N79A | RHS N77C and RHS 148A |
| Outer Leaves (At Harvest) | | | | | | | |
| Number of Leaves per Plant | | | 40 | 50 | 50 | 18 | 60 |
| Width (at Midpoint of plant including petiole) | cm | | 22.0 | 18.0 | 14.0 | 20.0 | 21.0 |
| Length (at midpoint of plant including petiole) | cm | | 30.0 | 22.0 | 22.0 | 30.0 | 30.0 |
| Petiole Length | cm | | 28.0 | 15.0 | 13.0 | 24.0 | 28.0 |
| Leaf Ratio-Length/Width | 1 = (2:1)<br>2 = (3:1)<br>3 = (4:1)<br>4 = (5:1)<br>5 = (6:1) | | 1 | 1 | 1 | 1 | 1 |
| Leaf Attachment | 1 = Sessile<br>2 = Petiolate<br>3 = Sessile and Petiolate | | 2 | 2 | 2 | 2 | 2 |
| Wax Presence | 1 = None<br>2 = Weak<br>3 = Intermediate<br>4 = Strong | | 3 | 4 | 3 | 3 | 3 |
| Foliage Color (with wax if present) | 1 = Light Green<br>2 = Medium Green<br>3 = Dark Green<br>4 = Grey-Green<br>5 = Blue-Green<br>6 = Purple-Green | | 5 | 6 | 6 | 6 | 6 |
| Foliage Color (upper) | Color Chart Name and Color Chart Code | | Closest to, but darker than RHS 133A | RHS 139A | RHS 139A | RHS 139A | RHS 139A |
| Foliage Color (lower) | Color Chart Name and Color Chart Code | | Closest to RHS N138A | RHS 137A | RHS N138C | RHS 138C | RHS N138B |

TABLE 2A-continued

| | | | | | | |
|---|---|---|---|---|---|---|
| Leaf Shape | 1 = Narrow Elliptic<br>2 = Elliptic<br>3 = Broad Elliptic | 3 | 2 | 1 | 2 | 2 |
| Leaf Base | 1 = Blunt<br>2 = Pointed | 1 | 1.5 | 1 | 1 | 1 |
| Leaf Apex | 1 = Blunt<br>2 = Pointed | 1 | 1 | 1 | 1 | 1 |
| Leaf Margins | 1 = Straight<br>2 = Slightly Wavy<br>3 = Very Wavy | 3 | 2 | 2 | 3 | 2 |
| Leaf Veins | 1 = Thin<br>2 = Intermediate<br>3 = Thick | 3 | 2 | 1 | 2 | 2 |
| Midrib | 1 = Not Raised<br>2 = Slightly Raised<br>3 = Raised | 3 | 3 | 2 | 2 | 2 |
| Blistering | 1 = None<br>2 = Weak<br>3 = Intermediate<br>4 = Strong | 4 | 3 | 3 | 3 | 3 |
| Attitude (Leaf Angle from Ground) | 1 = Horizontal (0-15 degrees)<br>3 = Semi-erect (35-55 degrees)<br>5 = Erect (80-100 degrees) | 3 | 5 | 5 | 3 | 3 |
| Torsion of Leaf Tip | 1 = None<br>2 = Weak<br>3 = Intermediate<br>4 = Strong | 4 | 2 | 3 | 4 | 3 |
| Profile of Upper Side of Leaf Head (At Market Maturity) | 1 = Concave<br>2 = Planar<br>3 = Convex | 1 | 2 | 1 | 1 | 1 |
| Diameter (at widest point) | cm | 14.0 | 12.0 | 11.0 | 16.0 | 14.0 |
| Depth | cm | 16.0 | 11.0 | 11.0 | 9.0 | 13.0 |
| Head Color | 1 = Light Green<br>2 = Medium Green<br>3 = Dark Green<br>4 = Blue-Green<br>5 = Purple<br>6 = Other | 5 | 5 | 4 | 6 | 4 |
| Head Color | Color Chart Name and Color Chart Code | RHS N187A and RHS N138A | Closest to but lighter than RHS N187A with RHS 137B | RHS N138B with slight RHS 79A | RHS N138B with slight RHS 79C | RHS N138B with slight RHS 79A |
| Head Shape | 1 = Circular<br>2 = Transverse Broad Elliptic<br>3 = Transverse Elliptic<br>4 = Transverse Elliptic Narrow | 4 | 4 | 4 | 4 | 4 |
| Dome Shape | 1 = Domed<br>2 = Semi-domed<br>3 = Deep Domed | 1 | 1 | 1 | 1 | 1 |
| Head Size | 1 = Small<br>2 = Medium<br>3 = Large | 2 | 1 | 1 | 3 | 2 |
| Compactness | 1 = Long Pedicels (Loose)<br>2 = Medium<br>3 = Short Pedicels (tight) | 3 | 1 | 1 | 2 | 2 |
| Surface Knobbling | 1 = Fine<br>2 = Medium<br>3 = Coarse | 2 | 3 | 3 | 2 | 2 |
| Bead Size | 1 = Small<br>2 = Medium<br>3 = Large | 2 | 3 | 3 | 1 | 3 |
| Flower Buds | 1 = Even in size<br>2 = Uneven in size (cateye) | 2 | 2 | 2 | 2 | 2 |

TABLE 2A-continued

| | | | | | | |
|---|---|---|---|---|---|---|
| Anthocyanin Coloration 1 = Absent 2 = Present | Leaf Axils | 1 | 1 | 1 | 1 | 1 |
| | Leaf Veins | 2 | 2 | 2 | 2 | 2 |
| | Leaf Blade | 1 | 1 | 1 | 1 | 1 |
| | Entire Plant | 2 | 2 | 2 | 2 | 2 |
| | Leaf Petiole | 2 | 2 | 2 | 2 | 2 |
| Color of Head Leaves | 1 = White 2 = Green 3 = Red 4 = Purple 5 = Other | 5 | 4 | 4 | 4 | 2 |
| Color of Head Leaves (upper) | Color Chart Name and Color Chart Code | Closest to but darker than RHS 133A | RHS 139A | RHS 139A | RHS 139A | RHS 139A |
| Color of Head Leaves (lower) | Color Chart Name and Color Chart Code | Closest to but darker than RHS N138A | RHS N138C | RHS N138C | RHS N138C | RHS N138C |
| Secondary Heads | 1 = Completely absent 2 = Basal 3 = Combination 4 = Axillary along entire main stem up to main head | 4 | 4 | 4 | 2 | 3 |
| Prominence of Secondary Heads | 1 = Weak 2 = Intermediate 3 = Strong | 1 | 3 | 3 | 1 | 3 |
| Number of Secondary Heads | | 4 | 10 | 9 | 2 | 19 |
| Flower | | | | | | |
| Flower Color | 1 = White 2 = Cream 3 = Yellow 4 = other | 3 | 3 | 3 | 3 | 3 |
| Flower Color | Color Chart Name and Color Chart Code | RHS 4B | RHS 4B | RHS 4B | RHS 10B | RHS 3B |
| Flower Stalk Color | 1 = Green 2 = Purple 3 = Variegated | 2 | 2 | 2 | 2 | 2 |
| Flower Stalk Color | Color Chart Name and Color Chart Code | RHS N187A | RHS 148A with slight RHS N79C | RHS 148A with slight RHS N79C | RHS N79A | RHS 148A and RHS N77C |
| Disease/ Insect/ Physiological Resistance | | Unknown | Unknown | Unknown | Unknown | Unknown |

| | | Variety | | | |
|---|---|---|---|---|---|
| | | 12KA077 (Purple baby broccoli; plot 41531) | 12KA069 (Purple baby broccoli) | K4-706 (Purple baby broccoli) | Santee |
| Region of Adaptation | | | | | |
| 1 = Northwest 2 = North Central 3 = Northeast 4 = Southeast 5 = Southwest 6 = Most Regions 7 = Pacific Coast 8 = Other | | 6 | 6 | 6 | 6 |
| Location and year of Data Collection | | Salinas 2014 | Salinas 2014 | Salinas 2014 | Salinas 2014 |
| Species | Species name | B. oleracea | B. oleracea | B. oleracea | B. oleracea |
| Maturity | | | | | |
| Harvest Season | 1 = Fall 2 = Fall/Winter 3 Winter/Spring 4 = Spring/Summer 5 = Summer 6 = Summer/Fall | 4 | 4 | 4 | 4 |

TABLE 2A-continued

| | | | | | |
|---|---|---|---|---|---|
| Spring Planted | Days from Direct Seeding to 50% Harvest | 90 | 85 | 85 | 115 |
| | Days from Transplanting to 50% Harvest | 55 | 50 | 55 | 80 |
| | Length of Harvest Period in days | 10 | 10 | 10 | 30 |
| Time of beginning of flowering | 1 = Early<br>2 = Medium-Early<br>3 = Medium<br>4 = Medium-Late<br>5 = Late | 3 | 2 | 2 | 5 |
| Plant (At Harvest) | | | | | |
| Plant Height (from soil line to top of leaves) | cm | 60.0 | 53.0 | 74.0 | 72.0 |
| Head Height (from soil line to top of head) | cm | 36.0 | 33.0 | 55.0 | 40.0 |
| Plant Branches | 1 = Few<br>2 = Medium<br>3 = Many | 1 | 2 | 1 | 3 |
| Branch Number | Total number of branches | 18 | 24 | 12 | 20 |
| Plant Habit | 1 = Spreading<br>2 = Intermediate<br>3 = Compact | 2 | 2 | 2 | 2 |
| Market Class | 1 = Fresh Market<br>2 = Processing<br>3 = Both | 1 | 1 | 3 | 1 |
| Life Cycle | 1 = Annual<br>2 = Biennial<br>3 = Perennial | 1 | 1 | 1 | 1.5 |
| Type of Variety | 1 = Inbred<br>2 = Open-Pollinated<br>3 = First Generation Hybrid | 3 | 3 | 3 | 3 |
| Stem Number | Total number of stems | 12 | 18 | 25 | 100 |
| Stem Length | cm | 7.0 | 6.0 | 7.0 | 10.0 |
| Stem Diameter | cm | 1.0 | 1.0 | 1.5 | 1.0 |
| Stem Color | Color Chart Name and Color Chart Code | RHS N79A with slight RHS 148A | RHS 148A with slight RHS N79C | RHS N187A | RHS 145A, head stems have both RHS 145A and RHS N187A |
| Outer Leaves (At Harvest) | | | | | |
| Number of Leaves per Plant | | 24 | 24 | 23 | 36 |
| Width (at Midpoint of plant including petiole) | cm | 24.0 | 22.0 | 20.0 | 14.0 |
| Length (at midpoint of plant including petiole) | cm | 32.0 | 30.0 | 29.0 | 40.0 |
| Petiole Length | cm | 30.0 | 20.0 | 24.0 | 17.0 |
| Leaf Ratio-Length/Width | 1 = (2:1)<br>2 = (3:1)<br>3 = (4:1)<br>4 = (5:1)<br>5 = (6:1) | 1 | 1 | 1.5 | 2.9 |
| Leaf Attachment | 1 = Sessile<br>2 = Petiolate<br>3 = Sessile and Petiolate | 2 | 2 | 2 | 2 |

TABLE 2A-continued

| | | | | | |
|---|---|---|---|---|---|
| Wax Presence | 1 = None<br>2 = Weak<br>3 = Intermediate<br>4 = Strong | 3 | 3 | 3 | 3 |
| Foliage Color (with wax if present) | 1 = Light Green<br>2 = Medium Green<br>3 = Dark Green<br>4 = Grey-Green<br>5 = Blue-Green<br>6 = Purple-Green | 6 | 6 | 6 | 2 |
| Foliage Color (upper) | Color Chart Name and Color Chart Code | RHS 139A | RHS 139A | Closest to, but darker than RHS 133A | RHS 139A |
| Foliage Color (lower) | Color Chart Name and Color Chart Code | RHS N138C | RHS N138C | Closest to RHS N138A | RHS 137A |
| Leaf Shape | 1 = Narrow Elliptic<br>2 = Elliptic<br>3 = Broad Elliptic | 2 | 2 | 2 | 1 |
| Leaf Base | 1 = Blunt<br>2 = Pointed | 1.5 | 1 | 1 | 1 |
| Leaf Apex | 1 = Blunt<br>2 = Pointed | 1 | 1 | 1 | 1 |
| Leaf Margins | 1 = Straight<br>2 = Slightly Wavy<br>3 = Very Wavy | 3 | 2 | 2 | 3 |
| Leaf Veins | 1 = Thin<br>2 = Intermediate<br>3 = Thick | 2 | 2 | 2 | 2 |
| Midrib | 1 = Not Raised<br>2 = Slightly Raised<br>3 = Raised | 2 | 2 | 1 | 1 |
| Blistering | 1 = None<br>2 = Weak<br>3 = Intermediate<br>4 = Strong | 3 | 3 | 1 | 1 |
| Attitude (Leaf Angle from Ground) | 1 = Horizontal (0-15 degrees)<br>3 = Semi-erect (35-55 degrees)<br>5 = Erect (80-100 degrees) | 5 | 3 | 3 | 3 |
| Torsion of Leaf Tip | 1 = None<br>2 = Weak<br>3 = Intermediate<br>4 = Strong | 4 | 3 | 1 | 1 |
| Profile of Upper Side of Leaf Head (At Market Maturity) | 1 = Concave<br>2 = Planar<br>3 = Convex | 1 | 1 | 2 | 1 |
| Diameter (at widest point) | cm | 15.0 | 15.0 | 13.0 | NA |
| Depth | cm | 12.0 | 13.0 | 27.0 | NA |
| Head Color | 1 = Light Green<br>2 = Medium Green<br>3 = Dark Green<br>4 = Blue-Green<br>5 = Purple<br>6 = Other | 6 | 5 | 5 | NA |
| Head Color | Color Chart Name and Color Chart Code | RHS N138B with slight RHS 79A | RHS N138B with slight RHS 79A | N79A (or N92A) | NA |
| Head Shape | 1 = Circular<br>2 = Transverse Broad Elliptic<br>3 = Transverse Elliptic<br>4 = Transverse Elliptic Narrow | 4 | 4 | 1 | NA |
| Dome Shape | 1 = Domed<br>2 = Semi-domed<br>3 = Deep Domed | 1 | 1 | 3 | NA |
| Head Size | 1 = Small<br>2 = Medium<br>3 = Large | 2 | 2 | 2 | NA |

TABLE 2A-continued

| | | | | | |
|---|---|---|---|---|---|
| Compactness | 1 = Long Pedicels (Loose)<br>2 = Medium<br>3 = Short Pedicels (tight) | 2 | 2 | 1 | NA |
| Surface Knobbling | 1 = Fine<br>2 = Medium<br>3 = Coarse | 2 | 2 | 2 | NA |
| Bead Size | 1 = Small<br>2 = Medium<br>3 = Large | 2 | 2 | 2 | NA |
| Flower Buds | 1 = Even in size<br>2 = Uneven in size (cateye) | 2 | 2 | 1 | NA |
| Anthocyanin Coloration<br>1 = Absent<br>2 = Present | Leaf Axils | 1 | 1 | 2 | 1.5 |
| | Leaf Veins | 2 | 2 | 2 | 1.5 |
| | Leaf Blade | 1 | 1 | 2 | 1.2 |
| | Entire Plant | 2 | 2 | 2 | 1.2 |
| | Leaf Petiole | 2 | 2 | 2 | 1.5 |
| Color of Head Leaves | 1 = White<br>2 = Green<br>3 = Red<br>4 = Purple<br>5 = Other | 5 | 4 | 2 | 2 |
| Color of Head Leaves (upper) | Color Chart Name and Color Chart Code | RHS 139A | RHS 139A | NA | NA |
| Color of Head Leaves (lower) | Color Chart Name and Color Chart Code | RHS N138C | RHS N138C | 136B | 136B |
| Secondary Heads | 1 Completely absent<br>2 = Basal<br>3 = Combination<br>4 = Axillary along entire main stem up to main head | 2 | 4 | 1 or 5 | 4 |
| Prominence of Secondary Heads | 1 = Weak<br>2 = Intermediate<br>3 = Strong | 2 | 1 | 1 | 3 |
| Number of Secondary Heads | | 12 | 6 | 1 | 17 |
| Flower | | | | | |
| Flower Color | 1 = White<br>2 = Cream<br>3 = Yellow<br>4 = other | 3 | 3 | 3 | 3 |
| Flower Color | Color Chart Name and Color Chart Code | RHS 10B | RHS 3B | RHS 5B | RHS 4B |
| Flower Stalk Color | 1 = Green<br>2 = Purple<br>3 = Variegated | 2 | 2 | 2 | NA |
| Flower Stalk Color | Color Chart Name and Color Chart Code | RHS N79A with slight RHS 148A | RHS 148A with slight RHS N79A | RHS N92D | RHS 143A |
| Disease/ Insect/ Physiological Resistance | | Unknown | Unknown | Unknown | Unknown |

TABLE 2B

| | Variety | | | | |
|---|---|---|---|---|---|
| | K1-703 (Purple baby broccoli) | Aspabroc (baby broccoli) | CMS H669 | H669 | 194-6-2 |
| Region of Adaptation | | | | | |
| 1 = Northwest 2 = North Central<br>3 = Northeast 4 = Southeast | 6 | 6 | 6 | 6 | 6 |

TABLE 2B-continued

| | | Salinas 2014 | Salinas 2014 | Salinas 2014 | Salinas 2014 | Salinas 2014 |
|---|---|---|---|---|---|---|
| 5 = Southwest 6 = Most Regions | | | | | | |
| 7 = Pacific Coast 8 = Other | | | | | | |
| Location and year of Data Collection | | | | | | |
| Species | Species name | *B. oleracea* | *B. oleracea* | *B. oleracea* | *B. oleracea* | *B. oleracea* |
| Maturity | | | | | | |
| Harvest Season | 1 = Fall<br>2 = Fall/Winter<br>3 Winter/Spring<br>4 = Spring/Summer<br>5 = Summer<br>6 = Summer/Fall | 5 | 4 | 4 | 4 | 4 |
| Spring Planted | Days from Direct Seeding to 50% Harvest | 85 | 80 | 95 | 95 | 70 |
| | Days from Transplanting to 50% Harvest | 55 | 50 | 60 | 60 | 60 |
| | Length of Harvest Period in days | 10 | 10 | 10 | 10 | 10 |
| Time of beginning of flowering | 1 = Early<br>2 = Medium-Early<br>3 = Medium<br>4 = Medium-Late<br>5 = Late | 2 | 1 | 4 | 4 | 1 |
| Plant (At Harvest) | | | | | | |
| Plant Height (from soil line to top of leaves) | cm | 60.0 | 60.0 | 38.0 | 29.0 | 55.0 |
| Head Height (from soil line to top of head) | cm | 40.0 | 49.0 | 28.0 | 26.0 | 45.0 |
| Plant Branches | 1 = Few<br>2 = Medium<br>3 = Many | 2 | 3 | 2 | 2 | 2 |
| Branch Number | Total number of branches | 22 | 50 | 36 | 30 | 15 |
| Plant Habit | 1 = Spreading<br>2 = Intermediate<br>3 = Compact | 2 | 1 | 1 | 1 | 2 |
| Market Class | 1 = Fresh Market<br>2 = Processing<br>3 = Both | 1 | 1 | 1 | 1 | 1 |
| Life Cycle | 1 = Annual<br>2 = Biennial<br>3 = Perennial | 1 | 1 | 1 | 1 | 1 |
| Type of Variety | 1 = Inbred<br>2 = Open-Pollinated<br>3 = First Generation Hybrid | 3 | 3 | 1 | 1 | 1 |
| Stem Number | Total number of stems | 10 | 25 | 8 | 6 | 20 |
| Stem Length | cm | 6.0 | 18.0 | 19.0 | 6.0 | 20.0 |
| Stem Diameter | cm | 1.6 | 1.5 | 1.5 | 1.5 | 1.4 |
| Stem Color | Color Chart Name and Color Chart Code | RHS N187A | RHS 146B | RHS 144A | RHS 144A | RHS 143A |
| Outer Leaves (At Harvest) | | | | | | |
| Number of Leaves per Plant | | 40 | 60 | 60 | 60 | 40 |
| Width (at Midpoint of plant including petiole) | cm | 22.0 | 16.0 | 15.0 | 19.0 | 13.0 |
| Length (at midpoint of plant including petiole) | cm | 30.0 | 24.0 | 19.0 | 23.0 | 18.0 |
| Petiole Length | cm | 28.0 | 27.0 | 22.0 | 30.0 | 10.0 |

TABLE 2B-continued

| | | | | | | |
|---|---|---|---|---|---|---|
| Leaf Ratio-Length/Width | 1 = (2:1)<br>2 = (3:1)<br>3 = (4:1)<br>4 = (5:1)<br>5 = (6:1) | 1 | 1 | 1 | 1 | 1 |
| Leaf Attachment | 1 = Sessile<br>2 = Petiolate<br>3 = Sessile and Petiolate | 2 | 2 | 2 | 3 | 2 |
| Wax Presence | 1 = None<br>2 = Weak<br>3 = Intermediate<br>4 = Strong | 3 | 3 | 3 | 3 | 2 |
| Foliage Color (with wax if present) | 1 = Light Green<br>2 = Medium Green<br>3 = Dark Green<br>4 = Grey-Green<br>5 = Blue-Green<br>6 = Purple-Green | 5 | 3 | 4 | 4 | 3 |
| Foliage Color (upper) | Color Chart Name and Color Chart Code | Closest to, but darker than RHS 133A | RHS 139A | RHS 139A | RHS 139A | RHS 147A |
| Foliage Color (lower) | Color Chart Name and Color Chart Code | Closest to RHS N138A | RHS 137A | RHS N138B | RHS N138B | RHS 147B |
| Leaf Shape | 1 = Narrow Elliptic<br>2 = Elliptic<br>3 = Broad Elliptic | 3 | 2 | 3 | 3 | 2 |
| Leaf Base | 1 = Blunt<br>2 = Pointed | 1 | 1 | 1 | 1 | 1 |
| Leaf Apex | 1 = Blunt<br>2 = Pointed | 1 | 1 | 1 | 1 | 1 |
| Leaf Margins | 1 = Straight<br>2 = Slightly Wavy<br>3 = Very Wavy | 3 | 2 | 3 | 3 | 2 |
| Leaf Veins | 1 = Thin<br>2 = Intermediate<br>3 = Thick | 3 | 3 | 1 | 1 | 2 |
| Midrib | 1 = Not Raised<br>2 = Slightly Raised<br>3 = Raised | 3 | 3 | 2 | 2 | 2 |
| Blistering | 1 = None<br>2 = Weak<br>3 = Intermediate<br>4 = Strong | 4 | 2 | 2 | 2 | 2 |
| Attitude (Leaf Angle from Ground) | 1 = Horizontal (0-15 degrees)<br>3 = Semi-erect (35-55 degrees)<br>5 = Erect (80-100 degrees) | 3 | 3 | 2 | 2 | 3 |
| Torsion of Leaf Tip | 1 = None<br>2 = Weak<br>3 = Intermediate<br>4 = Strong | 4 | 3 | 4 | 4 | 3 |
| Profile of Upper Side of Leaf Head (At Market Maturity) | 1 = Concave<br>2 = Planar<br>3 = Convex | 1 | 1.5 | 3 | 3 | 1.5 |
| Diameter (at widest point) | cm | 14.0 | 15.0 | 14.0 | 14.0 | 16.0 |
| Depth | cm | 16.0 | 18.0 | 9.0 | 6.0 | 20.0 |
| Head Color | 1 = Light Green<br>2 = Medium Green<br>3 = Dark Green<br>4 = Blue-Green<br>5 = Purple<br>6 = Other | 5 | 4 | 2 | 2 | 4 |
| Head Color | Color Chart Name and Color Chart Code | RHS N187A and RHS N138A | RHS N138A | RHS N138A and RHS 144A | RHS N138A and RHS 144 A | RHS N138A |
| Head Shape | 1 = Circular<br>2 = Transverse Broad Elliptic | 4 | 4 | 4 | 4 | 4 |

TABLE 2B-continued

|  |  |  |  |  |  |  |
|---|---|---|---|---|---|---|
|  | 3 = Transverse Elliptic |  |  |  |  |  |
|  | 4 = Transverse Elliptic Narrow |  |  |  |  |  |
| Dome Shape | 1 = Domed | 1 | 2 | 2 | 2 | 1 |
|  | 2 = Semi-domed |  |  |  |  |  |
|  | 3 = Deep Domed |  |  |  |  |  |
| Head Size | 1 = Small | 2 | 2 | 2 | 2 | 2 |
|  | 2 = Medium |  |  |  |  |  |
|  | 3 = Large |  |  |  |  |  |
| Compactness | 1 = Long Pedicels (Loose) | 3 | 2 | 3 | 3 | 1 |
|  | 2 = Medium |  |  |  |  |  |
|  | 3 = Short Pedicels (tight) |  |  |  |  |  |
| Surface Knobbling | 1 = Fine | 2 | 2 | 2 | 2 | 3 |
|  | 2 = Medium |  |  |  |  |  |
|  | 3 = Coarse |  |  |  |  |  |
| Bead Size | 1 = Small | 2 | 2 | 2 | 2 | 3 |
|  | 2 = Medium |  |  |  |  |  |
|  | 3 = Large |  |  |  |  |  |
| Flower Buds | 1 = Even in size | 2 | 1 | 2 | 2 | 2 |
|  | 2 = Uneven in size (cateye) |  |  |  |  |  |
| Anthocyanin Coloration 1 = Absent 2 = Present | Leaf Axils | 1 | 1 | 1 | 1 | 1 |
|  | Leaf Veins | 2 | 1 | 1 | 1 | 1 |
|  | Leaf Blade | 1 | 1 | 1 | 1 | 1 |
|  | Entire Plant | 2 | 1 | 1 | 1 | 1 |
|  | Leaf Petiole | 2 | 2 | 1 | 1 | 1 |
| Color of Head Leaves | 1 = White | 5 | 2 | 2 | 2 | 2 |
|  | 2 = Green |  |  |  |  |  |
|  | 3 = Red |  |  |  |  |  |
|  | 4 = Purple |  |  |  |  |  |
|  | 5 = Other |  |  |  |  |  |
| Color of Head Leaves (upper) | Color Chart Name and Color Chart Code | Closest to but darker than RHS 133A | RHS 139A | RHS 139A | RHS 139A | RHS 139A |
| Color of Head Leaves (lower) | Color Chart Name and Color Chart Code | Closest to but darker than RHS N138A | RHS 137A | RHS N138B | RHS N138B | RHS 138A |
| Secondary Heads | 1 = Completely absent | 4 | 4 | 4 | 4 | 4 |
|  | 2 = Basal |  |  |  |  |  |
|  | 3 = Combination |  |  |  |  |  |
|  | 4 = Axillary along entire main stem up to main head |  |  |  |  |  |
| Prominence of Secondary Heads | 1 = Weak | 1 | 3 | 1 | 1 | 1 |
|  | 2 = Intermediate |  |  |  |  |  |
|  | 3 = Strong |  |  |  |  |  |
| Number of Secondary Heads |  | 4 | 13 | 2 | 4 | 8 |
| Flower |  |  |  |  |  |  |
| Flower Color | 1 = White | 3 | 3 | 3 | 3 | 3 |
|  | 2 = Cream |  |  |  |  |  |
|  | 3 = Yellow |  |  |  |  |  |
|  | 4 = other |  |  |  |  |  |
| Flower Color | Color Chart Name and Color Chart Code | RHS 4B | RHS 4B | RHS 4B | RHS 4B | RHS 5A |
| Flower Stalk Color | 1 = Green | 2 | 1 | 1 | 1 | 1 |
|  | 2 = purple |  |  |  |  |  |
|  | 3 = Variegated |  |  |  |  |  |
| Flower Stalk Color | Color Chart Name and Color Chart Code | RHS N187A | RHS 146B | RHS 144A | RHS 144A | RHS 143B |
| Disease/ Insect/ Physiological Resistance |  | Unknown | Unknown | Unknown | Unknown | Unknown |

TABLE 2B-continued

| | | Variety | | | |
|---|---|---|---|---|---|
| | | 12KA069 (Purple baby broccoli; plot 41538) | 12KA075sis (Purple baby broccoli; plot 41539) | 12KA077 (Purple baby broccoli; plot 41540) | Purple Peacock |
| Region of Adaptation | | | | | |
| 1 = Northwest 2 = North Central 3 = Northeast 4 = Southeast 5 = Southwest 6 = Most Regions 7 = Pacific Coast 8 = Other | | 6 | 6 | 6 | 6 |
| Location and year of Data Collection | | Salinas 2014 | Salinas 2014 | Salinas 2014 | Salinas 2014 |
| Species | Species name | *B. oleracea* | *B. oleracea* | *B. oleracea* | *B. oleracea* |
| Maturity | | | | | |
| Harvest Season | 1 = Fall 2 = Fall/Winter 3 Winter/Spring 4 = Spring/Summer 5 = Summer 6 = Summer/Fall | 4 | 4 | 4 | 4 |
| Spring Planted | Days from Direct Seeding to 50% Harvest | 85 | 90 | 90 | 90 |
| | Days from Transplanting to 50% Harvest | 50 | 55 | 55 | 60 |
| | Length of Harvest Period in days | 10 | 10 | 10 | 20 |
| Time of beginning of flowering | 1 = Early 2 = Medium-Early 3 = Medium 4 = Medium-Late 5 = Late | 2 | 3 | 3 | 3 |
| Plant (At Harvest) | | | | | |
| Plant Height (from soil line to top of leaves) | cm | 75.0 | 65.0 | 82.0 | 60.0 |
| Head Height (from soil line to top of head) | cm | 55.0 | 50.0 | 56.0 | 39.0 |
| Plant Branches | 1 = Few 2 = Medium 3 = Many | 2 | 3 | 2 | 1 |
| Branch Number | Total number of branches | 30 | 20 | NA | 25 |
| Plant Habit | 1 = Spreading 2 = Intermediate 3 = Compact | 2 | 1 | 2 | 3 |
| Market Class | 1 = Fresh Market 2 = Processing 3 = Both | 3 | 3 | 3 | 1 |
| Life Cycle | 1 = Annual 2 = Biennial 3 = Perennial | 1 | 1 | 1 | 1 |
| Type of Variety | 1 = Inbred 2 = Open-Pollinated 3 = First Generation Hybrid | 3 | 3 | 3 | 2 |
| Stem Number | Total number of stems | 15 | 18 | 10 | 18 |
| Stem Length | cm | 6.0 | 10.0 | 6.0 | 8.0 |
| Stem Diameter | cm | 1.0 | 1.0 | 1.0 | 1.0 |
| Stem Color | Color Chart Name and Color Chart Code | RHS 148A with slight RHS N79C | RHS N77C and RHS 148A | RHS N79A with slight RHS 148A | RHS N187A |
| Outer Leaves (At Harvest) | | | | | |
| Number of Leaves per Plant | | 20 | 23 | 23 | 28 |

TABLE 2B-continued

| | | | | | |
|---|---|---|---|---|---|
| Width (at Midpoint of plant including petiole) | cm | 15.0 | 20.0 | 22.0 | 12.0 |
| Length (at midpoint of plant including petiole) | cm | 23.0 | 28.0 | 32.0 | 27.0 |
| Petiole Length | cm | 14.0 | 20.0 | 23.0 | 15.0 |
| Leaf Ratio-Length/Width | 1 = (2:1)<br>2 = (3:1)<br>3 = (4:1)<br>4 = (5:1)<br>5 = (6:1) | 1.5 | 1.4 | 1.5 | 2.3 |
| Leaf Attachment | 1 = Sessile<br>2 = Petiolate<br>3 = Sessile and Petiolate | 2 | 2 | 2 | 2 |
| Wax Presence | 1 = None<br>2 = Weak<br>3 = Intermediate<br>4 = Strong | 3 | 3 | 3 | 2 |
| Foliage Color (with wax if present) | 1 = Light Green<br>2 = Medium Green<br>3 = Dark Green<br>4 = Grey-Green<br>5 = Blue-Green<br>6 = Purple-Green | 6 | 6 | 6 | 6 |
| Foliage Color (upper) | Color Chart Name and Color Chart Code | RHS 139A | RHS 139A | RHS 139A | RHS 137B with RHS N187A blotches |
| Foliage Color (lower) | Color Chart Name and Color Chart Code | RHS N138C | RHS N138B | RHS N138C | RHS 137C with RHS N187A blotches |
| Leaf Shape | 1 = Narrow Elliptic<br>2 = Elliptic<br>3 = Broad Elliptic | 2 | 3 | 2 | 1 |
| Leaf Base | 1 = Blunt<br>2 = Pointed | 1 | 1 | 1 | 1 |
| Leaf Apex | 1 = Blunt<br>2 = Pointed | 1 | 1 | 1 | 2 |
| Leaf Margins | 1 = Straight<br>2 = Slightly Wavy<br>3 = Very Wavy | 3 | 2 | 2 | 3 |
| Leaf Veins | 1 = Thin<br>2 = Intermediate<br>3 = Thick | 2 | 2 | 2 | 2 |
| Midrib | 1 = Not Raised<br>2 = Slightly Raised<br>3 = Raised | 1 | 2 | 2 | 2 |
| Blistering | 1 = None<br>2 = Weak<br>3 = Intermediate<br>4 = Strong | 1 | 1 | 1 | 1 |
| Attitude (Leaf Angle from Ground) | 1 = Horizontal (0-15 degrees)<br>3 = Semi-erect (35-55 degrees)<br>5 = Erect (80-100 degrees) | 3 | 2 | 2 | 2 |
| Torsion of Leaf Tip | 1 = None<br>2 = Weak<br>3 = Intermediate<br>4 = Strong | 3 | 3 | 1 | 1 |
| Profile of Upper Side of Leaf Head (At Market Maturity) | 1 = Concave<br>2 = Planar<br>3 = Convex | 2 | 2 | 2 | 2 |
| Diameter (at widest point) | cm | 16.0 | 16.0 | 16.0 | 8.0 |
| Depth | cm | 25.0 | 18.0 | 16.0 | 6.0 |
| Head Color | 1 = Light Green | 5 | 5 | 5 | 5 |

TABLE 2B-continued

| | | | | | |
|---|---|---|---|---|---|
| | 2 = Medium Green | | | | |
| | 3 = Dark Green | | | | |
| | 4 = Blue-Green | | | | |
| | 5 = Purple | | | | |
| | 6 = Other | | | | |
| Head Color | Color Chart Name and Color Chart Code | RHS N79A (or N92A) | RHS N79A (or N92A) | RHS N79A (or N92A) | RHS N79A (or N92A) |
| Head Shape | 1 = Circular | 1 | 1 | 1 | 1 |
| | 2 = Transverse Broad Elliptic | | | | |
| | 3 = Transverse Elliptic | | | | |
| | 4 = Transverse Elliptic Narrow | | | | |
| Dome Shape | 1 = Domed | 3 | 3 | 3 | 2 |
| | 2 = Semi-domed | | | | |
| | 3 = Deep Domed | | | | |
| Head Size | 1 = Small | 2 | 2 | 2 | 1 |
| | 2 = Medium | | | | |
| | 3 = Large | | | | |
| Compactness | 1 = Long Pedicels (Loose) | 1 | 1 | 2 | 2 |
| | 2 = Medium | | | | |
| | 3 = Short Pedicels (tight) | | | | |
| Surface Knobbling | 1 = Fine | 2 | 2 | 2 | 2 |
| | 2 = Medium | | | | |
| | 3 = Coarse | | | | |
| Bead Size | 1 = Small | 2 | 3 | 2 | 2 |
| | 2 = Medium | | | | |
| | 3 = Large | | | | |
| Flower Buds | 1 = Even in size | 1 | 1 | 1 | 2 |
| | 2 = Uneven in size (cateye) | | | | |
| Anthocyanin Coloration 1 = Absent 2 = Present | Leaf Axils | 2 | 1 | 1 | 2 |
| | Leaf Veins | 2 | 1 | 1 | 2 |
| | Leaf Blade | 2 | 1 | 1 | 2 |
| | Entire Plant | 2 | 1 | 1 | 2 |
| | Leaf Petiole | 2 | 1 | 1 | 2 |
| Color of Head Leaves | 1 = White | 2 | 2 | 2 | 2 |
| | 2 = Green | | | | |
| | 3 = Red | | | | |
| | 4 = Purple | | | | |
| | 5 = Other | | | | |
| Color of Head Leaves (upper) | Color Chart Name and Color Chart Code | NA | NA | NA | NA |
| Color of Head Leaves (lower) | Color Chart Name and Color Chart Code | RHS 136B | RHS 136A | RHS 136A | RHS 135A |
| Secondary Heads | 1 = Completely absent | 5 | 5 | 5 | 5 |
| | 2 = Basal | | | | |
| | 3 = Combination | | | | |
| | 4 = Axillary along entire main stem up to main head | | | | |
| Prominence of Secondary Heads | 1 = Weak | 2 | 3 | 2 | 1 |
| | 2 = Intermediate | | | | |
| | 3 = Strong | | | | |
| Number of Secondary Heads | | 7 | 14 | 8 | 2 |
| Flower | | | | | |
| Flower Color | 1 = White | 3 | 3 | 3 | 3 |
| | 2 = Cream | | | | |
| | 3 = Yellow | | | | |
| | 4 = other | | | | |
| Flower Color | Color Chart Name and Color Chart Code | RHS 5B | RHS 5B | RHS 5B | RHS 5B |
| Flower Stalk Color | 1 = Green | 2 | 2 | 2 | 2 |
| | 2 = purple | | | | |
| | 3 = Variegated | | | | |
| Flower Stalk Color | Color Chart Name and Color Chart Code | RHS N92A | RHS N92A | RHS N92A | RHS 148A with slight RHS N79B |

TABLE 2B-continued

| | | | | |
|---|---|---|---|---|
| Disease/Insect/Physiological Resistance | Unknown | Unknown | Unknown | Unknown |

Purple baby broccoli, such as purple baby broccoli K1-703, K4-706, 12KA075sis, 12KA077 and 12KA069, is most similar to traditional baby broccoli (Aspabroc) and variety Purple Peacock. When purple baby broccoli is compared to baby broccoli, as shown in Tables 1 and 2B, purple baby broccoli K1-703 has a purple stem color of RHS N187A, wider leaves with an average width of 22 cm, a blue-green foliage color, broad elliptic leaves, a purple head color and short pedicels, whereas baby broccoli has a green stem color of RHS 146B, thinner leaves with an average width of 16 cm, a dark green foliage color, elliptic leaves, a blue-green head color and medium pedicels. When purple baby broccoli is compared to Purple Peacock, also as shown in Tables 1 and 2B, purple baby broccoli K1-703 has wider leaves with an average width of 22 cm, a blue-green foliage color, broad elliptic leaves, a purple head color of RHS N187A and N138A, short pedicels and purple head leaves, whereas Purple Peacock has thinner leaves with an average width of 12-15 cm, purple-green foliage, narrow elliptic leaves, a head color closest to RHS N187A with some RHS 137A, or N79 (or N92A), medium pedicels and green head leaves.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

Deposits of the Sakata Seed America, Inc. proprietary *Brassica oleracea* CMS AS001P, AS001P, CMS AS002P, and AS002P disclosed above have been made with the American Type Culture Collection (ATCC), 10801 University Boulevard, Manassas, Va. 20110 under the terms of the Budapest Treaty. The date of deposits was Feb. 7, 2018. The deposits of 2,625 seeds were taken from the same deposits maintained by Sakata Seed America, Inc. since prior to the filing date of this application. All restrictions will be irrevocably removed upon granting of a patent, and the deposits are intended to meet all of the requirements of 37 C.F.R. §§ 1.801-1.809. The ATCC Accession Numbers are PTA-124869, PTA-124867, PTA-124870 and PTA-124868, respectively. The deposits will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A method for producing a seed of a baby broccoli plant comprising the steps of:
    (a)(i) crossing a CMS AS001P broccoli plant with an AS001P broccoli plant, wherein a representative sample of seed of said CMS AS001P broccoli plant was deposited under ATCC Accession No. PTA-124869 and wherein a representative sample of seed of said AS001P broccoli line was deposited under ATCC Accession No. PTA-124867; or
    (ii) crossing a CMS AS001P broccoli plant with an AS002P broccoli plant, wherein a representative sample of seed of said AS002P broccoli line was deposited under ATCC Accession No. PTA-124868; or
    (iii) crossing a CMS AS002P broccoli plant with an AS001P broccoli plant, wherein a representative sample of seed of said CMS AS002P broccoli plant was deposited under ATCC Accession No. PTA-124870; or
    (iv) crossing a CMS AS002P broccoli plant with an AS002P broccoli plant; and
    (b) allowing seed of a broccoli plant to form.

2. The method of claim 1, wherein said method further comprises growing said broccoli seed to yield a baby broccoli plant.

* * * * *